(12) United States Patent
Pitcovski et al.

(10) Patent No.: US 10,821,179 B2
(45) Date of Patent: Nov. 3, 2020

(54) PROTEINS MODIFIED WITH (AMINO) MONOSACCHARIDE-BIOTIN ADDUCT

(71) Applicants: Jacob Pitcovski, Korazim (IL); Jacob Vaya, Merom Hagalil (IL); Soliman Khatib, Ramat Hagolan (IL); Elina Aizenshtein, Arad (IL); Tal Gefen, Karmiel (IL)

(72) Inventors: Jacob Pitcovski, Korazim (IL); Jacob Vaya, Merom Hagalil (IL); Soliman Khatib, Ramat Hagolan (IL); Elina Aizenshtein, Arad (IL); Tal Gefen, Karmiel (IL)

(73) Assignee: GAVISH-GALILEE BIO APPLICATIONS, LTD., Kiryat Shmona (IL)

( * ) Notice: Subject to any disclaimer, the term of this patent is extended or adjusted under 35 U.S.C. 154(b) by 330 days.

(21) Appl. No.: 14/932,040

(22) Filed: Nov. 4, 2015

(65) Prior Publication Data

US 2016/0120977 A1    May 5, 2016

Related U.S. Application Data

(63) Continuation of application No. 13/376,070, filed as application No. PCT/IL2010/000446 on Jun. 6, 2010, now abandoned.

(60) Provisional application No. 61/184,113, filed on Jun. 4, 2009.

(51) Int. Cl.
| | |
|---|---|
| *A61K 39/44* | (2006.01) |
| *A61K 8/60* | (2006.01) |
| *A61K 47/55* | (2017.01) |
| *A61K 47/54* | (2017.01) |

(52) U.S. Cl.
CPC ............ *A61K 39/44* (2013.01); *A61K 47/549* (2017.08); *A61K 47/551* (2017.08)

(58) Field of Classification Search
None
See application file for complete search history.

(56) References Cited

U.S. PATENT DOCUMENTS

| | | | |
|---|---|---|---|
| 5,856,571 | A | 1/1999 | Berninger et al. |
| 5,948,624 | A | 9/1999 | Rothschild et al. |
| 2007/0060497 | A1 | 3/2007 | Krahmer et al. |
| 2008/0108129 | A1 | 5/2008 | Pitcovski et al. |

FOREIGN PATENT DOCUMENTS

| | | |
|---|---|---|
| JP | 2005226021 A | 8/2005 |
| WO | 2006050247 A2 | 5/2006 |
| WO | 2006070371 A2 | 7/2006 |

OTHER PUBLICATIONS

Giuliano Elia ("Elia", Proteomics, 2008, 8, 4012-4024).*
Velander et al.("Velander", Biotech & Bioeng. 1992, 39, 1024-1030).*
Lin et al. ("Lin", Tet. Lett, 1997, 38, 15, 2649-2652).*
Kupper, Beilstein Journal of Organic Chemistry, vol. 8, p. 712-725, 2012.
Musiani, et al., Mannose receptor determination by an ELISA-like method, J. Biochem. Biophys. Methods, 2003, pp. 121-125, vol. 55.
International Search Report from PCT/IL2010/000446, dated Oct. 22, 2010.
Sanchez et al., Toxicon, vol. 41, p. 315-320, 2003.
Vaya et al. Vaccine, vol. 27, p. 6869-6876, 2009.
Sigma-Aldrich, www.signaaldrich.com/catalog/ProductDetail.do?D7=0&N5=SE . . . , A7924, Albumin, bovine-α-D-mannopyranosylphenyl isothiocyanate-biotin labeled lyophilized powder, 2010.

* cited by examiner

*Primary Examiner* — Karl J Puttlitz
*Assistant Examiner* — Kauser M Akhoon
(74) *Attorney, Agent, or Firm* — Browdy and Neimark, P.L.L.C.

(57) ABSTRACT

A protein, e.g. an antibody, coated with a non-immunogenic molecule selected from an amino-monosaccharide-biotin adduct or a monosaccharide-biotin adduct is disclosed, wherein the coated protein, which has diminished immunogenicity relative to the uncoated protein and intact biological activity, enables, for example, cross-species vaccination.

**10 Cla

PROTEINS MODIFIED WITH (AMINO) MONOSACCHARIDE-BIOTIN ADDUCT

TECHNICAL FIELD

Figure 1:
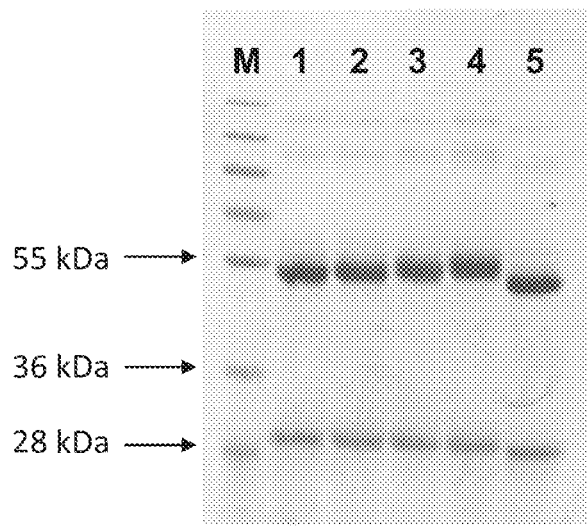

The present invention relates to proteins modified with monosaccharide-biotin adducts, and in particular to modified antibodies with reduced antigenicity.

BACKGROUND ART

Antibodies have been used for the prevention and treatment of infectious diseases for over a century. Antibody therapy is used in the modern arsenal of antimicrobial therapeutics (Keller and Stiehm, 2000; Oral et al., 2002; Buchwald and Pirofski, 2003) and in the therapy of viral diseases (Keller ant Stiehm, 2000; Law and Hangartner, 2008). Additionally, new applications were suggested for passive immunization, e.g. in treatment of neurological disorders and cancer. Furthermore, antibodies are still a superior therapeutic choice for toxin neutralization and remain a critical component of the treatment for diphtheria, tetanus, botulism and snake envenomation.

Passive immunization can be achieved by intravenous (i.v.) or intramuscular (i.m.) administration of antibodies as plasma or serum, as pooled immunoglobulin from immunized or convalescing donors, and as monoclonal antibodies. There are several obstacles in utilization of passive immunization in human medicine: 1. The treatment requires antibodies of the same species in order to avoid anti-isotype immune reaction; 2. shortage of suitable hyperimmune donors; 3. batch-to-batch variations; 4. the risk of pathogen transmission; 5. production cost of sufficient quantities of high quality antibodies; and 6. the occurrence of serum sickness.

Obviously, the cheapest and most available source to produce antibodies is animal plasma or serum. However, passive vaccination with antibodies extracted from animal serum is inefficient due to their antigenicity and possible adverse effects, such as the potentially fatal anaphylactic shock and serum sickness. In some cases, the solution to this problem has been to use fragmented (F(ab')2 or Fab) immunoglobulins (IgG) or humanized antibodies. Despite significant progress in minimizing immune responses they still occur, even against fully human antibodies. Additionally, such modifications involve time-consuming research and development, and are limited to the identification of monoepitopes.

Reduction of protein immunogenicity, alteration of the protein's surface properties and increase of the plasma half-life is presently achieved mainly by Polyethylene Glycol (PEG) (for example Gaberc-Porekar et al., 2008) and Dextran or Dextran derivatives of various molecular weights (for example (Kobayashi et al., 2001; Mehvar, 2003).

The use of mannose or oleic acid and mannose for obtaining a modified protein or viruses with maintained antigen binding and decreased antigenicity relative to unmodified protein or viruses, respectively, has been described previously by the inventors (WO 2006/070371). Harris et al., 2003 discloses proteins modified with linoleic acid and linoleic dicarboxylic acid, and Ong et al., 1991 have reported galactose modified antibodies that are quickly cleared from the blood via the asialoglycoprotein receptor.

SUMMARY OF INVENTION

The present invention provides a protein, such as an antibody, covalently linked to a non-immunogenic molecule selected from an amino-monosaccharide-biotin adduct or a monosaccharide-biotin adduct. In certain embodiments, the protein is an antibody covalently linked to 2-amino-mannose-biotin adduct.

The invention further relates to pharmaceutical compositions comprising said antibodies. In one embodiment, the pharmaceutical composition comprises an anti-tumor associated antigen antibody such as Trastuzumab. In other embodiments, the pharmaceutical composition comprises an anti-virus antibody or anti-bacterium antibody or an anti-snake venom antibody.

BRIEF DESCRIPTION OF DRAWINGS

FIG. 1 shows an SDS-PAGE gel of hIgG coated with different amounts of amino-mannose-biotin adduct (MBA). Equal amounts of hIgG (1 mg in 1 ml of 25 mM PB, pH 6 were reacted with 20 (lane 1), 80 (lane 2), 300 (lane 3) or 1000 (lane 4) μg of MBA for 3 h and changes in hIgG size after modification with MBA were determined. Lane 5, control hIgG without modification. M, molecular weight markers.

FIG. 2 shows detection of coated hIgG with secondary antibodies by western blot analysis. Equal amounts of hIgG were reacted with 80, 300 or 1000 μg MBA. The samples were subjected to 15% SDS-PAGE and recognition of the coated hIgG was determined by applying secondary antibody on a western blot.

FIG. 3 shows the immune response in chickens to hIgG coated with different amounts of MBA. Coated/uncoated hIgG was injected i.m., and Ab production was examined by ELISA. 20 μg, Ab against hIgG from chickens injected with hIgG-$MBA^{20}$ (20 μg of MBA/mg hIgG); 80 μg, Ab against hIgG from chickens injected with hIgG-$MBA^{80}$ (80 μg of MBA/mg hIgG); 300 μg, Ab against hIgG from chickens injected with hIgG-$MBA^{300}$ (300 μg of MBA/mg hIgG); 1000 μg, Ab against hIgG from chickens injected with hIgG-$MBA^{1000}$ (1000 μg of MBA/mg of hIgG); hIgG, Ab against hIgG from chickens injected with uncoated hIgG; Neg. control, Ab against hIgG in non-injected chickens. Inset: serum dilutions. Results are shown as bars+ SD. *$p \le 0.0003$, $P \le 0.001$ or *$P \le 0.02$ for the difference in Ab level against hIgG between chickens treated with coated and uncoated hIgG.

FIGS. 4A-B shows the immune response in chickens to hIgG coated with MBA or PEG. Injection of coated hIgG with (A) and without Freund's adjuvant (B). Antigens were injected i.m. and Ab production against hIgG was examined by ELISA. MBA, Ab against hIgG from chickens injected with hIgG-$MBA^{1000}$; PEG, Ab against hIgG from chickens injected with hIgG-PEG; hIgG, Ab against hIgG from chickens injected with uncoated hIgG; Neg. control, Ab against hIgG in non-injected chickens. Inset: serum dilutions. Representative results of two experiments (one repeat in experiment 4A and three repeats in 4B) are shown as bars+ SD. *$P \le 0.0003$ or $P \le 0.002$ for differences in Ab level against hIgG between chickens treated with hIgG-$MBA^{1000}$ and hIgG. **$P \le 0.001$ or *$P \le 0.03$ for the differences in Ab level against hIgG between hIgG-PEG- and hIgG-treated chickens.

FIG. 5 shows the immune response in chickens to molecules used for the various coated hIgGs. Antigen was injected i.m. and Ab against molecules used to coat the various modified hIgGs were examined by ELISA. MBA, Ab against MBA from chickens injected with hIgG-MBA; PEG, Ab against PEG from chickens injected with hIgG-PEG; hIgG, Ab against hIgG from chickens injected with uncoated hIgG; Neg. control, Ab against coated or uncoated hIgG from non-injected chickens. Inset: serum dilutions. **P≤0.002 for the differences in Ab level against hIgG between sera from chickens injected with hIgG and sera from non-treated chickens. Results are presented as bars±SD.

Figure 6A:
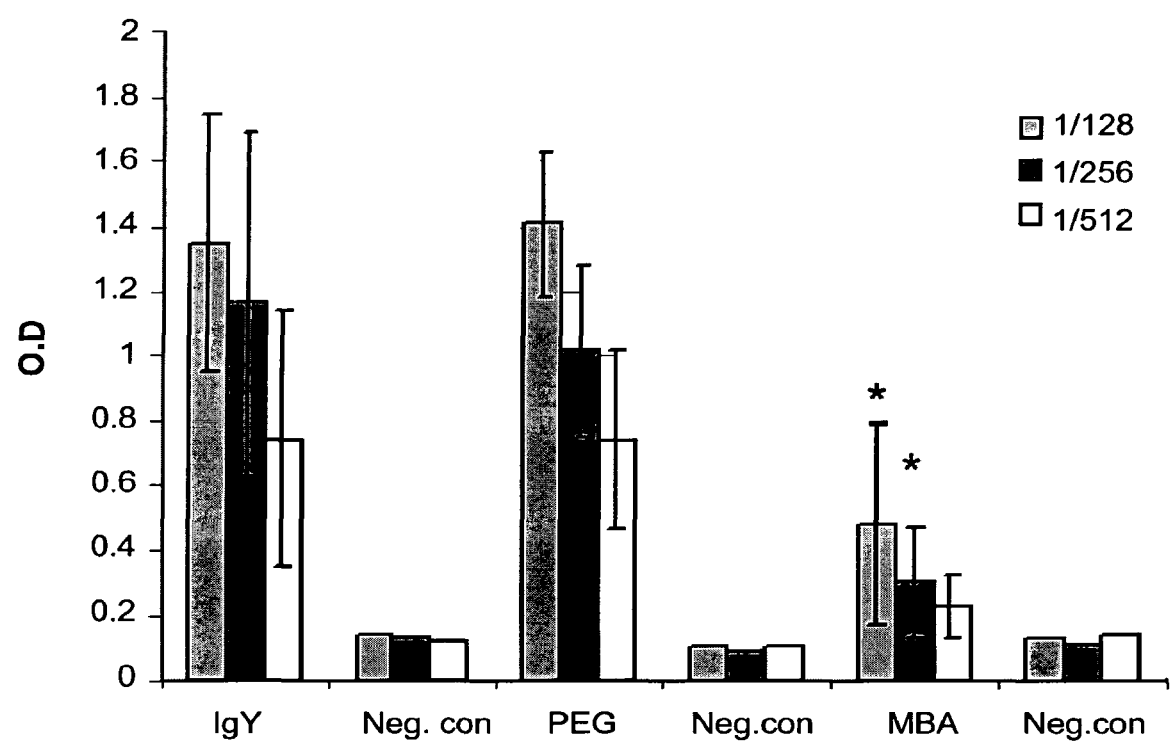
Figure 6B:
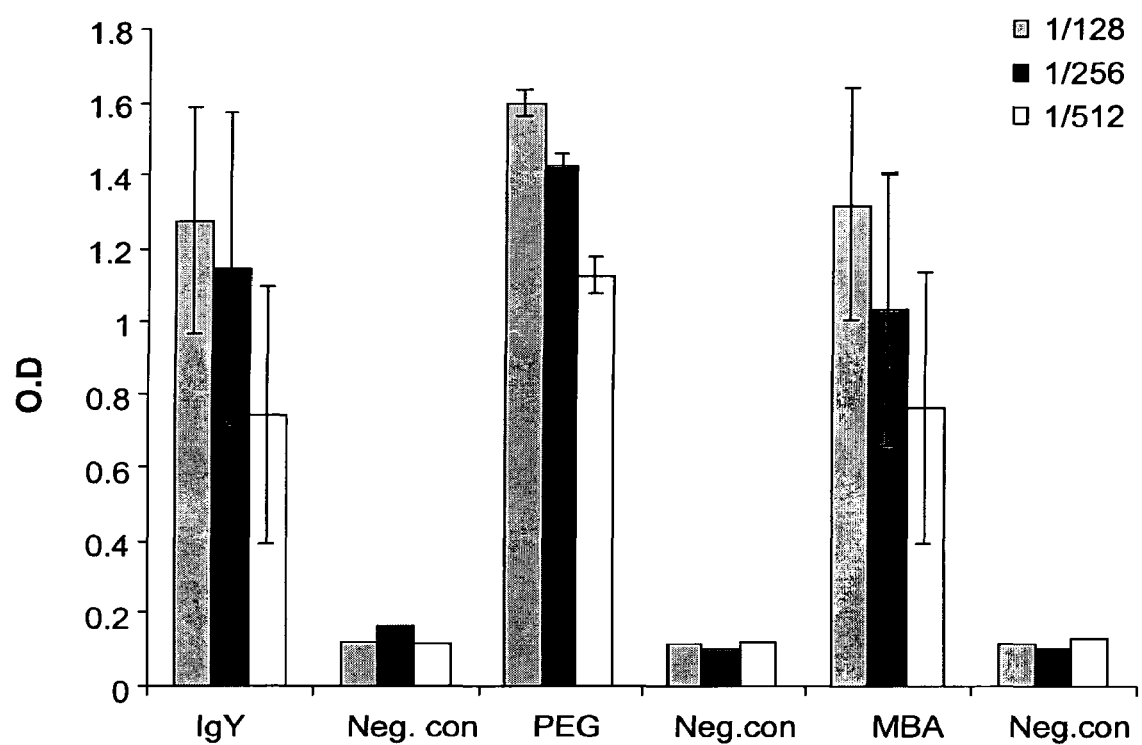

FIGS. 6A-B show immunological response to IgY and IgY modified with PEG or MBA in mice, following two IV (A) or IM (B) injections. Neg. Con.—Non-injected mice.

Figure 7A:
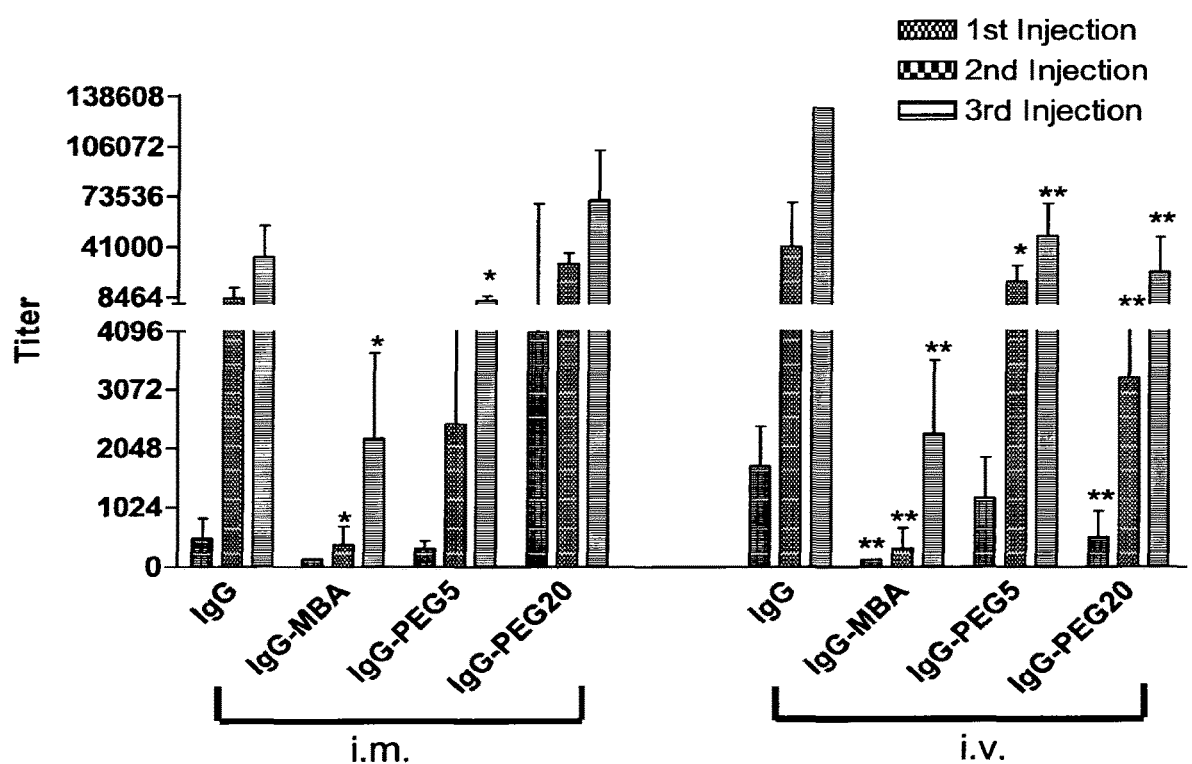
Figure 7B:
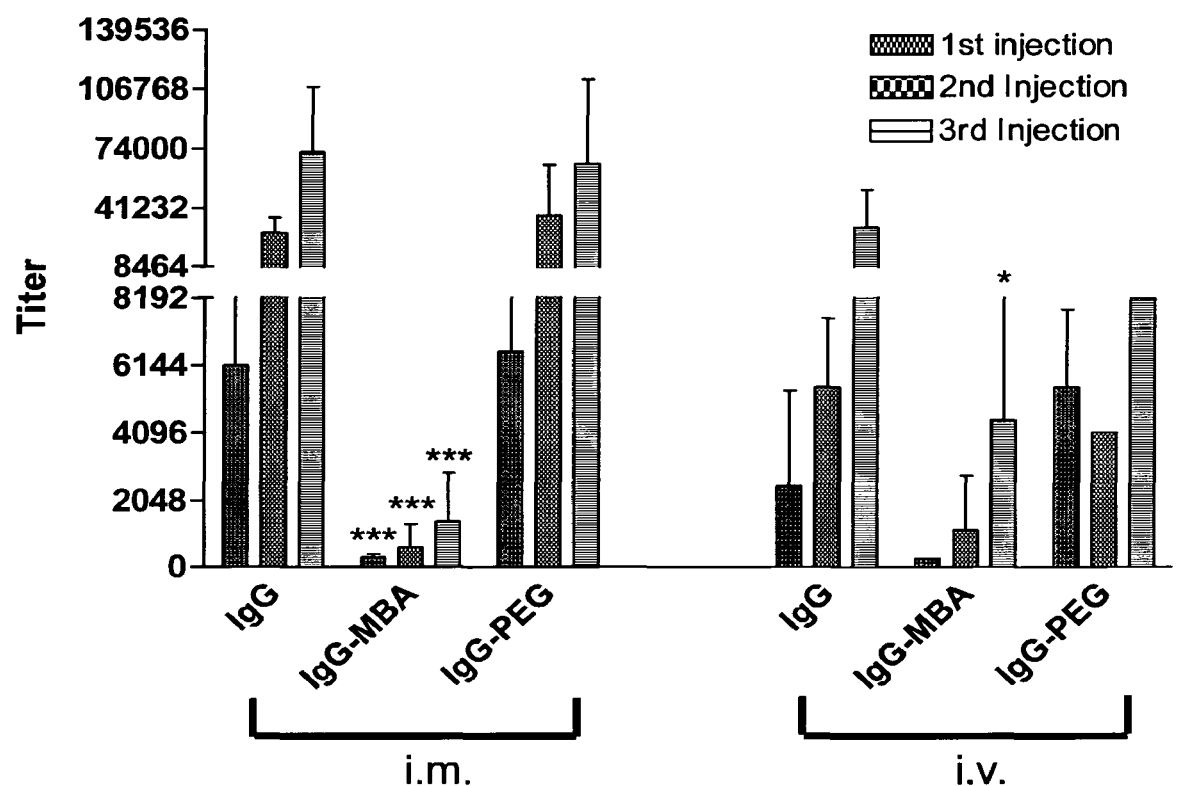

FIGS. 7A-B show the ability of MBA masked molecules to reduce humoral immune response in different mouse strains. Horse IgG (hsIgG), hsIgG-MBA or hsIgG-PEG was injected into Balb/c (A) or C57BL6 mice (B) i.m. or i.v. three times, at a 2-week interval. Immunized mice sera were tested by ELISA, using unmodified hsIgG as antigen. The titer was determined as the reciprocal value of 2 fold serial dilution end point (×2 of negative control OD value), of tested serum. Results are shown as bars±SD. *p<0.001, P<0.01 or *P<0.05 for the difference in antibodies titer against horse IgG between mice treated with masked and unmasked horse IgG.

Figure 8:
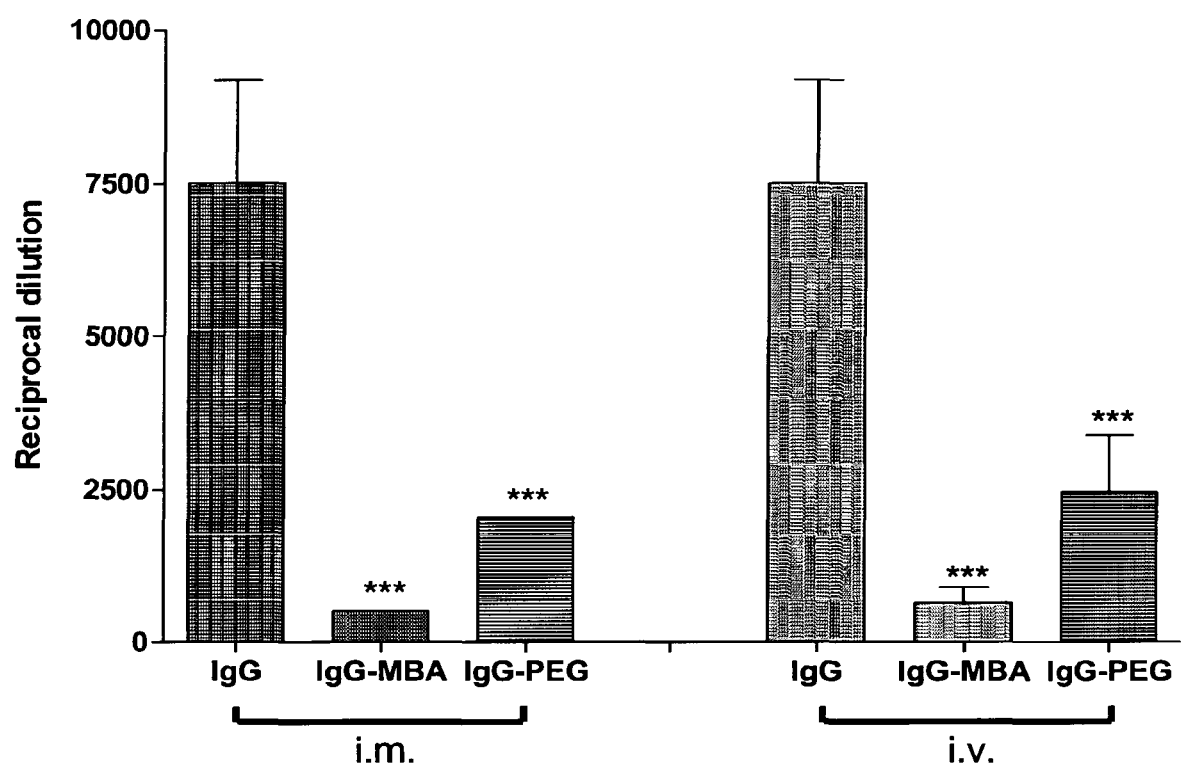

FIG. 8 shows immune response against IgG following sequential dose treatment. Horse IgG, IgG-MBA or horse IgG-PEG were injected into Balb/c mouse i.m. or i.v. three times during three days, giving a total amount of 200 μg of antigen per mouse. Immune response was evaluated after two weeks. Results are shown as bars±SD. *p<0.001 for the difference in Ab level against horse IgG between mice treated with masked and unmasked horse IgG FIG. 9** shows recognition of antigen-bound hIgG-$MBA^{1000}$ by monocytic THP-1 cells through their Fc receptor. An ELISA plate was coated with tetanus toxin antigen, followed by incubation with anti-tetanus toxin hIgG or hIgG-$MBA^{1000}$. Then, fluorescent THP-1 cells were added to the wells for various periods of time. The fluorescence level was determined by fluorometer. hIgG, monocyte cell binding efficiency to uncoated hIgG; hIgG-$MBA^{1000}$, monocyte cell binding efficiency to coated hIgG (1 mg hIgG reacted with 1000 μg of MBA); Neg. control, tetanus toxin incubated with fluorescent monocytic cells without hIgG. Inset: incubation times. *P≤0.05 for the difference between monocyte binding efficiency to hIgG vs. hIgG-$MBA^{1000}$. Representative values of three independent experiments are shown as bars±SD FIG. 10 shows a hemagglutination test in which inhibition activity of coated IgY is demonstrated. IgY, uncoated antibodies; PEG, IgY coated with PEG; MBA, IgY coated with MBA.

FIG. 11 shows determination of multivalent antigen detection by coated/uncoated anti-venom. Two μg of venom per lane were subjected to Western blot, and reacted with 20 μg IgG and developed with mouse anti horse IgG-horseradish peroxidase (HRP) conjugate (lane 1) or reacted with 20 μg IgG-MBA and developed with avidin-HRP conjugate (lane 2). MW, molecular weight (kDa).

FIG. 12 depicts the effect of masking an antibody on its binding affinity. 10 μg IgG HRP conjugate were mixed with various concentrations (100 μg/ml-97 ng/ml) (X axis) of IgG, IgG-MBA or IgG-PEG. The mixes were incubated in an ELISA plate coated with venom as antigen. The plate was developed with OPD and OD monitored at 450 nm. Representative values from three independent experiments are shown.

FIG. 13 shows in vitro venom inhibition. Inhibition of venom proteolitic enzyme, tested by azocoll. The dye monitored by optical density reads at 550 nm and is represented as percent of inhibition. Pre-incubated venom with hsIgG, hsIgG-MBA or hsIgG-PEG were added to azocoll for 2 hours incubation. Results are shown as bars±SD, for the difference between 3 independent tests.

FIG. 14 shows in vivo venom inhibition. 2×LD50 doses of venom were pre-incubated with IgG or masked IgG and injected i.v. into balb/c mice. Percent of survival represent mouse which survived 48 hours after injection. Results are shown as means of 4 independent tests. Each symbol represent the percent survival of a group of 6 mice.

FIG. 15 depicts an experiment measuring the effect of coating of Trastuzumab (referred to as herceptin) with MBA on the binding affinity of the antibody using a competitive ELISA. 10 μg Trastuzumab-fluorescein conjugate were mixed with various concentrations (100 μg/ml-97 ng/ml) (X axis) of herceptin or herceptin-MBA. 10 μg herceptin-fluorescein conjugate were mixed with various concentrations (100 μg/ml-97 ng/ml) (X axis) of herceptin, herceptin-MBA or herceptin-PEG. The mixes were incubated in 96 wells tissue culture, optic bottom, plate coated with fixated SKBR-3 cells as antigen. The fluorescein units were detected and shows as Mean Fluorescent Units (MFU). Results are shown as XY point's±SD. Representative values from three independent experiments are shown.

FIG. 16 depicts the effect of coated/uncoated anti-HER2 (referred to as herceptin) on the viability of HER2+ SK-BR3 or BT 474 breast cancer cells. Cells were grown with 10 μg/ml of coated/uncoated herceptin and compared to cells alone (cells alone correspondent to 100% viability). Results are shown as scatter plot, each point represents a single independent experiment and horizontal line represents mean values.

DETAILED DESCRIPTION OF THE INVENTION

One of the problems encountered in the administration of foreign molecules to an organism is their antigenicity. Foreign molecules, e.g., antibodies, that are produced in another species and used for passive vaccination, induce an immune response in the host and cannot be used repeatedly.

The present invention provides masked proteins, preferably antibodies, with decreased or eliminated antigenicity. Modified antibodies according to the present invention enable cross-species vaccination. For example, therapeutic murine, chimeric or humanized monoclonal antibodies or human monoclonal antibodies that cause an immune response in a human host may be modified according to the present invention, thereby preventing, diminishing or eliminating the undesired immune responses. In another example, modified chicken- or horse-derived polyclonal antibodies against snake toxins can be used for vaccination of humans to treat snakebite envenomation.

In contrast to major published studies wherein proteins were masked using synthetic polymers or polysaccharides as masking agents, the present application discloses small endogenous molecules for masking the proteins or the viruses. The use of mannose and oleic acid for obtaining a modified protein or virus with an intact native binding site and decreased antigenicity has been described in WO 2006/070371 by the same inventors. In the present invention, the inventors set out to label the mannose with biotin, another endogenous molecule, in order to be able to follow the labeled protein, for example in order to establish the half-life of the modified protein after injection into an animal. It was a very surprising finding of the present invention that the amino-mannose-biotin adduct (MBA) was much more effective in reducing the immunogenicity than the unlabeled mannose molecule, especially since biotin, which is extensively used in the art of labeling proteins, has not been shown to reduce immunogenicity of proteins. As detailed in the Examples below, the biotin was, for technical reasons, linked to the 2-amino mannose via its 2-amino group. However, it could obviously also have been linked via one of the hydroxyl groups.

Thus, in one aspect, the invention relates to a protein, which is covalently linked to a non-immunogenic molecule selected from an amino-monosaccharide-biotin adduct or a monosaccharide-biotin adduct. The terms "amino-monosaccharide-biotin" and "monosaccharideamine-biotin" are used interchangeably herein.

The monosaccharide moiety of the amino-monosaccharide-biotin adduct or the monosaccharide-biotin adduct of the invention may be, but is not limited to, ketoses or aldoses of 3-6 carbon atoms, for example aldoses of 5-6 carbon atoms, in particular mannose. All mannoseamine isoforms are considered, such as a 1-amino-mannose, 2-amino-mannose, 3-amino-mannose, 4-amino-mannose, 5-amino-mannose, and 6-amino-mannose, and more preferably 2-amino-mannose. Similarly, the mannose-biotin adduct may be a mannose-2-biotin, mannose-3-biotin, mannose-4-biotin, mannose-5-biotin, or mannose-6-biotin isoform. In certain embodiments, the amino-monosaccharide-biotin adduct is 2-aminomannose-biotin.

The masking agent is preferentially reacted with functional groups of the protein to form covalent bonds. For example, amino-mannose-biotin, can react with the protein free carboxylic acid residues of aspartic or glutamic acid to form esters, or with the free amine groups of lysine or arginine. Such options allow controlling the desired degree of masking by choosing the type of amino acids residues of the protein or the virus surface to be bound, in order to reach the desired and most suitable reduction of the degree of immunogenicity. Moreover, the agent selected for masking the protein surface may be attached to molecules which target specific cells or tissues, and thus the modified protein, e.g. modified antibody, may be used to deliver this agent to the desired specific target.

Masking of the protein with amino-mannose-biotin can be performed, for example, in two steps: first, the free amino groups on the protein surface are masked by reaction with the aldehyde moiety of amino-mannose, followed by addition of a coupling reagent such as 1-ethyl-3-(3-dimethylaminopropyl) carbodiimide (EDC), to facilitate esterification of the free carboxyl groups on the protein surface with the mannose hydroxyl groups (Hermanson, G. T. (1995). Bioconjugate Techniques, Academic Press, Inc). In this way, two functional groups of the amino acid residues of the protein or the virus—amino and carboxyl groups—are protected to a degree that is related to the reaction conditions such as type of solvent used (protic, aprotic, polar, etc), type and amount of esterification catalyst used, e.g., EDC, p-toluenesulfonic acid (pTSA), and/or 4-(dimethylamino) pyridine (DMAP), the ratio between the reactants (protein/monosaccharide), reaction time, etc. The double bond of the imine group of the Schiff's base formed in the first step can be further reduced, for example, with NaH$_3$BCN, in order to increase the stability of the masked molecule.

In certain embodiments, the protein that is masked with, i.e. covalently linked to, a non-immunogenic molecule of the invention is an antibody. In certain embodiments, the masked antibody of the invention is (i) a humanized or chimeric monoclonal IgG antibody; (ii) a mammalian monoclonal IgG antibody; (iii) a mammalian polyclonal IgG antibody; or (iv) a chicken IgY antibody.

Indeed, it has been found in accordance with the present invention that chicken IgY, mouse, horse and human IgG and humanized monoclonal IgG antibodies can all be coated with MBA while retaining their binding affinity and biological activities and eliciting reduced immunological responses in foreign species as compared with uncoated antibodies. Thus, any antibody can be masked with MBA for the purpose of decreasing its immunogenicity. For example, Table 1 exhibits examples of currently FDA approved antibodies for treatment of a variety of diseases. Certainly these antibodies, but also other antibodies not mentioned here, can be coated with MBA and are therefore included in the scope of the present invention.

In particular, the antibody of the present invention is selected from an anti-tumor associated antigen antibody, an anti-snake venom antibody, an anti-virus antibody or an anti-bacterium antibody. For example, the anti-tumor antibody may be an anti-HER2 receptor HER-2/neu (human epidermal growth factor receptor-2) antibody, for example Trastuzumab which is shown in Example 11 to retain its HER2-binding properties when coated with MBA. However, the anti-tumor associated antigen antibody may be directed to any tumor associated antigen such as, but not limited to, alpha-fetoprotein, BA-46/lactadherin, BAGE (B antigen), BCR-ABL fusion protein, beta-catenin, CASP-8 (caspase-8), CDK4 (cyclin-dependent kinase 4), CEA (carcinoembryonic antigen), CRIPTO-1 (teratocarcinoma-derived growth factor), elongation factor 2, ETV6-AML1 fusion protein, G250/MN/CAIX, GAGE, gp100 gp100 (glycoprotein 100)/Pmel17, intestinal carboxyl esterase, KIAA0205, MAGE (melanoma antigen), MART-1/Melan-A (melanoma antigen recognized by T cells/melanoma antigen A), MUC-1 (mucin 1), N-ras, p53, PAP (prostate acid phosphatase), PSA (prostate specific antigen), PSMA (prostate specific membrane antigen), telomerase, TRP-1/gp75 (tyrosinase related protein 1, or gp75), TRP-2, tyrosinase, and uroplakin Ia, Ib, II and III.

The anti-snake venom antibody may be an antibody to *C. atrox* venom or viper venom. Both antibodies, when masked with MBA, are shown hereinafter to evoke a

TABLE 1

FDA-approved monoclonal antibodies for cancer treatment

| Main category | Name of drug | Type of cancer used to treat |
| --- | --- | --- |
| Anti cancer | Alemtuzumab (Campath) | Chronic lymphocytic leukemia |
| | Bevacizumab (Avastin) | Breast cancer; Colon cancer; Lung cancer |
| | Cetuximab (Erbitux) | Colon cancer; Head and neck cancers |
| | Gemtuzumab (Mylotarg) | Acute myelogenous leukemia |
| | Ibritumomab (Zevalin) | Non-Hodgkin's lymphoma |
| | Panitumumab (Vectibix) | Colon cancer |
| | Rituximab (Rituxan) | Non-Hodgkin's lymphoma |
| | Tositumomab (Bexxar) | Non-Hodgkin's lymphoma |
| | Trastuzumab (Herceptin) | Breast cancer |
| Anti-inflammatory | infliximab | Rheumatoid arthritis, Crohn's disease, ulcerative colitis |
| | adalimumab | Rheumatoid arthritis, Crohn's disease, ulcerative colitis |
| | etanercept | Rheumatoid arthritis |
| | basiliximab | Acute rejection of kidney transplants |
| | daclizumab | Acute rejection of kidney transplants |
| | omalizumab | Moderate-to-severe allergic asthma |

TABLE 1-continued

FDA-approved monoclonal antibodies for cancer treatment

| Main category | Name of drug | Type of cancer used to treat |
|---|---|---|
| Other | palivizumab | Respiratory syncytial virus infections in children |
| | abciximab | Prevent coagulation in coronary angioplasty |

Sources: FDA and wikipedia diminished immunological response in a host injected with these antibodies as compared with native antibodies, and to bind as efficiently and neutralize snake venom as well as unmasked antibodies in vitro and in vivo. The anti-viper antibody studied in the present invention is directed to *Vipera palaestinae* serum. An anti-influenza virus antibody coated with MBA is shown herein in Example 8 to be as efficient as an uncoated antibody in inhibiting hemagglutination of red blood cells.

Thus, in certain embodiments the anti-tumor associated antigen antibody is an anti-HER2 receptor antibody, the anti-snake venom antibody is an anti-*C. atrox* venom antibody or an anti-viper venom antibody, and the anti-virus antibody is an anti-influenza virus antibody. In particular, the anti-HER2 receptor antibody is Trastuzumab.

It has been found in accordance with the present invention that the immunogenicity of an IgG molecule is reduced if at least about 4 amino-mannose-biotin adduct molecules are covalently attached to each IgG antibody molecule. It has further been found that an increase in the molar ratio of amino-mannose-biotin adduct:IgG further reduces the antigenicity of the antibody, such that about 9-10 amino-mannose-biotin adduct molecules per IgG provide improved masking, i.e. further reduced immunogenicity, and 11-12 amino-mannose-biotin adduct molecules per IgG molecule provide optimal masking and almost completely abolishes the immunogenicity of the antibody. Thus, in one embodiment the ratio of amino-mannose-biotin adduct to IgG, or monosaccharide-biotin adduct to IgG antibody, is 4:1, 5:1, 6:1, 7:1, 8:1, 9:1, 10:1, 11:1 or 12:1, i.e. between about 4:1 and about 12:1. Since the number of free carboxyl groups in a protein is approximately similar to the number of amino groups in the same protein, and since carboxyl groups may easily be transformed to amino groups as detailed above, the number of MBA molecules that may be bound to an IgG antibody is twice that shown herein. Therefore, the ratio of amino-mannose-biotin adduct to IgG may be as high as about 24:1.

In certain embodiments, the molar ratio of amino-mannose-biotin adduct to IgG antibody, or monosaccharide-biotin adduct to IgG antibody, is between about 11:1 to about 12:1.

It is expected that the biotin moiety of the amino-monosaccharide-biotin adduct or monosaccharide-biotin adduct may be replaced with biotin-like molecules without affecting the ability of the adduct to reduce immunogenicity of proteins. Non-limiting examples of biotin-like molecules are diaminobiotin and desthiobiotin. Also molecules comprising an ureido (tetrahydroimidizalone) ring fused with a tetrahydrothiophene ring which is found in biotin, or analogs thereof such as those found in diaminobiotin and desthiobiotin, that are linked to the monosaccharide via a spacer replacing the valeric acid moiety of biotin, are considered. The spacer may be for example a hydrocarbyl group of 1 to about 50 carbon atoms in length, optionally interrupted by one or more heteroatoms selected from O, S or N, or one or more aromatic rings, or polyethylene glycol or a peptide of similar length. In addition biotin can be replaced by lipoic acid or lipoic acid derivatives and linked to monosaccharide or amino-monosaccharide.

As used herein, the term "antibodies" refers to polyclonal and monoclonal antibodies of avian, e.g. chicken, and mammals, including humans, and to fragments thereof such as F(ab')2 fragments of polyclonal antibodies, and Fab fragments and single-chain Fv fragments of monoclonal antibodies. The term also refers to chimeric, humanized and dual-specific antibodies.

The present invention further relates to a pharmaceutical composition comprising a protein according to the invention, and a pharmaceutically acceptable carrier. This pharmaceutical composition may be used for both prophylactic as well as therapeutic purposes As stated above, it has been shown herein that many kinds of antibodies can be masked with MBA without detrimental consequences to the binding or biological activity properties of the antibodies. Thus, the present invention is directed to any antibody approved for therapeutic use for treating a disease such as cancer, neurological disorders inflammation-related disease, autoimmune disease, an infectious disease or any other disease or disorder (see Table 1 for non-limiting examples), and masked with MBA.

In certain embodiments, the pharmaceutical composition of the present invention is for treating a cancer selected from breast cancer, chronic lymphocytic leukemia, colon cancer, head and neck cancers, lung cancer, acute myelogenous leukemia and non-Hodgkin's lymphoma. In particular, the pharmaceutical composition is for treating breast cancer and comprises an anti-HER2 receptor antibody, for example Trastuzumab.

In certain embodiments, the pharmaceutical composition of the present invention comprises an anti-virus antibody or anti-bacterium antibody. Thus, the pharmaceutical composition, in certain cases, comprises a vaccine for passive immunization in humans or animals against bacteria or for toxin neutralization in diphtheria, tetanus intoxication, botulism and snake envenomation, and they may be also useful for passive vaccination in humans or animals against viruses such as influenza, ebola, hepatitis respiratory syncytial virus, and avian influenza virus. In particular, the anti-virus antibody is an anti-influenza virus.

In another embodiment, the pharmaceutical composition comprises an anti-snake venom antibody, in particular an anti-*C. atrox* venom antibody or an anti-viper venom antibody.

The non-immunogenic molecules of the invention may also be applied to proteins associated with the surface of a virus, preferably with the viral capsid or with the envelope, thus rendering the virus less immunogenic and with intact binding to its natural binding receptors.

Adenovirus (Ad) is a group of nonenveloped double-stranded DNA viruses associated with a range of respiratory, ocular, and gastrointestinal infections. Entry of human Ad into human cells is a stepwise process. The primary event in this sequence is attachment that involves an interaction between the Ad fiber protein and its high-affinity cellular receptor. The Ad type 5 (Ad5) fiber is a homotrimer with each subunit consisting of three domains: the amino-terminal tail that associates with the penton base protein; the shaft, which consists of a motif of approximately 15 residues that is repeated 22 times; and the knob, which interacts with the cellular receptor.

A replication-defective adenovirus vector has been used for efficient delivery of DNA and is applicable in adenovirus-mediated gene delivery in gene targeting and gene therapy.

The present invention also contemplates a modified hormone such as parathyroid hormone (PTH) or human growth hormone (hGH) with a functional receptor-binding site, wherein the hormone surface is masked with non-immunogenic molecules, such as amino-mannose biotin, except for the protected receptor-binding site, and said masking provides the hormone with prolonged half-life in the body.

A further protein that may benefit from reduced immunogenicity is an enterotoxin such as the enterotoxin of *Escherichia coli* (LT) with a functional GM1 ganglioside receptor-binding site, or the cholera toxin of *Vibrio cholera* (CT) with a functional GM1 ganglioside receptor-binding site. The modified enterotoxin may be useful for delivery of molecules into cells via oral or skin routes.

The invention will now be illustrated by the following non-limiting Examples.

EXAMPLES

Materials and Methods

Materials.

Human (h) IgG was purified from the whole serum of patients immunized with tetanus toxoid (TT). 2-aminomannose, NaCNBH$_3$, MPEG-NHS (methoxy polyethyleneglycolsuccinate N-hydroxysuccinimide) and biotin were purchased from Sigma-Aldrich. Biotin-NHS was purchased from Pierce. Amicon ultra-centrifugal filter devices (MWCO 10,000 and 30,000) were purchased from Millipore. Trastuzumab was purchased from Roche.

Synthesis of Amino-Mannose-Biotin (MBA).

2-Aminomannose (70 mg, 0.39 mmol) was dissolved in 0.5 ml DMSO and biotin-NHS (100 mg, 0.3 mmol) was added. The solution was stirred at room temperature (RT) for 2 h. A new peak was formed as detected by HPLC at a retention time of 14 min (for details see HPLC analysis). The new peak was isolated and purified by flash chromatography (silica gel, methanol:ethyl acetate, 5:95 as solvents). Using conventional analytical methods, the pure product was identified as MBA. The LC-MS of the product, using positive ion monitoring mode (ES$^+$), revealed the expected molecular ion m/z of 406 (M+H$^+$) and fragmentations with m/z of 364.6 and 249.5, identical to previously reported data (Lin, Chun-Cheng et al., Tetrahedron left. 1997, 38, 2649).

HPLC Analysis of MBA.

The HPLC was connected to a diode array detector (HP-1100) and equipped with a reverse-phase column (C-18, 150 mm length; 4.6 mm diameter with 5 μm particles). The mobile phase was a mixture of acetonitrile and water which was run at a flow rate of 1 ml/min with the following gradient: acetonitrile from 1% to 5% over 5 min, and then to 20% for another 5 min and finally to 98% for an additional 10 min.

LC/MS/MS Analysis of MBA.

The product was injected into MS in a direct injection with scan, using the ESI$^+$ method. The source temperature of the MS was set at 150° C., with a cone gas flow of 22 l/h, a desolvation gas flow of 400 l/h and a capillary voltage of 3.5 KV. Peak spectra were monitored between 30 and 800 m/z.

Coating of MgG Antibody with MBA.

MBA (1 mg, 2.5 nmol in 60 μl DMSO) was added to hIgG (1 mg, 6.6 nmol in 1 ml of 25 mM phosphate buffer (PB), pH 6). The solution was mixed for 1 h at RT, and then NaCNBH$_3$ (2 mg, 32 μmol) was added and the reaction was continued for an additional 2 h at RT. Excess MBA reagent was discarded from the reaction solution by filtration through an Amicon ultra-centrifugal filter device with a MWCO of 10,000.

Controlling the Coating Reaction (MBA/hIgG Ratio).

Various amounts of MBA (20, 80, 300 and 1000 μg) from a stock solution of 25 mg in 1 ml DMSO were added to hIgG (1 mg hIgG in 1 ml of 25 mM (PB), pH 6) to monitor the ratio of MBA/hIgG (coating/coated ratio). The solution was mixed for 1 h at RT and different amounts of NaCNBH$_3$ (30, 120, 450 and 1500 μg from a stock solution of 17 mg NaCNBH$_3$ in 1 ml PBS) were added, respectively. The solution was left for another 2 h at RT. The excess MBA was then removed from the reaction mixture by filtration through an Amicon ultra-centrifugal filter device (MWCO 10,000). This filtrate was then taken for further analysis.

Coating hIgG with Methoxy-PEG-NHS.

MPEG-NHS (7 mg) was added to hIgG (1 mg in 1 ml PBS pH 7.4). The solution was mixed for 3 h at RT and then excess reagent was removed by filtration through an Amicon ultra-centrifugal filter device (MWCO 30,000). The filtrate was then taken for further analysis.

Number of Unbound Free Amino Groups in the Coated and Uncoated Protein.

The following procedure was based on a previous work (Vidal and Franci, 1986) with some modifications. Briefly, the coated and uncoated hIgG were reacted with TNBSA (trinitrobenzenesulfonic acid or picrylsulfonic acid). Under mild conditions, this reagent reacts specifically with free amino groups on the amino acid side chain of a protein to give trinitrophenyl (TNP) derivatives. Thus, 50 μg of hIgG (from a stock solution of 1 mg/ml in PBS) was added to 140 μl sodium tetraborate buffer (0.1 M, pH 9.3) in a 96-well plate. Aqueous TNBSA (10 μl of 0.01 M) was added and the solution was incubated for 30 min at 37° C. The absorption of the solution was measured at 405 nm in an ELISA reader (Lumitron) and the amount of free amine was calculated from a calibration curve prepared by reacting TNBSA with a known amount of glycine.

Gel Electrophoresis and Western Blot Analysis.

To determine changes in the size of hIgG after modification with various amounts of MBA, the samples were analyzed by SDS-PAGE. Gel electrophoresis was performed in a 15% polyacrylamide gel prepared in 1.5 M Tris HCl, pH 8.8. The pellets (10 μl) were mixed with loading buffer (0.5 M Tris HCl pH 6.8, 33% glycerol, 3% SDS, 5% mercaptoethanol, 0.5% bromophenol blue) and the samples were run at RT at 50 mA in 25 mM Tris base, 20 mM glycine, 0.1% SDS. The gel was stained with Coomassie blue or transferred to nitrocellulose for detection of modified hIgG with secondary antibody by western blot analysis. The membrane was blocked with PBS containing 0.5% Tween 20 and 5% dry milk (blocking buffer) for 1 h at 37° C. and incubated with a 1:5000 dilution of horseradish peroxidase (HRP)-conjugated goat anti-hIgG (Jackson ImmunoResearch Laboratories, Inc.) for 1 h at 37° C. in blocking buffer. After washes in PBS containing 0.5% Tween 20, bands were detected by enhanced chemiluminescence (ECL) (Pierce).

In-Vivo Trials.

1. Vaccination of birds—The effect of masking molecules was tested on laying hens, nine birds per group. The birds were injected i.m. with unmodified hIgG or hIgG modified with various amounts of MBA or PEG. Each bird was injected with 50 μg protein, twice at a 2-week interval. Blood was drawn 2 weeks after the second vaccine injection and sera were kept at −20° C. until analysis. The presence of antibodies in the sera was tested by ELISA using unmodified or modified hIgG as the antigen.

In addition, the immune response to hIgG or modified hIgG mixed with Freund's complete adjuvant (FCA) was examined in chickens. The birds, nine laying hens per group, were immunized i.m. with 50 μg of hIgG or hIgG modified with MBA/FCA or PEG/FCA mixture. Two weeks later, birds were reinjected in the same manner with the same amount of antigen in incomplete Freund's adjuvant (IFA). Blood was drawn 2 weeks after the second vaccination and sera were kept at −20° C. until analysis. The presence of antibodies in the sera was tested by ELISA using unmodified hIgG as the antigen.

2. Vaccination of mice—The effect of masking molecules was tested on Balb/c mouse, six rodents per group. Six mice per group were injected i.m. or i.v. with 50 μg of unmodified or modified horse IgG (hsIgG) with MBA or with PEG three times, at 2-week intervals. Two weeks after each injection, blood was drawn and serum was separated and sera were kept at/−20° C. until analysis.

For deferential dose treatment, each mouse was injected with 25 μg on day one, 75 μg on the second day and 100 μg on the third day, giving a total amount of 200 μg per mouse. Two weeks after the third injection, bloods were drawn and sera were kept at/−20° C. until analysis.

ELISA.

The presence of antibodies against hIgG in chicken or mouse sera following i.m. injection of unmodified hIgG or hIgG modified with different amounts of MBA or with PEG was tested by ELISA. Each of the following steps was followed by three washes with 0.05% Tween-20 in PBS and drying on a paper towel. ELISA plates (Nunc) were incubated overnight at 4° C. with hIgG diluted in carbonate-coating buffer (pH 9.6) to a final concentration of 5 to 8 μg/ml (for chicken) or 1 μg/ml (for mouse). Skim milk (5%) in PBS was added for 1 h at 37° C. as a blocking step. Then different serum dilutions were incubated for 1-2 h at 37° C., followed by incubation with a secondary antibody, rabbit anti-chicken IgG conjugated to HRP (Sigma), diluted 1:5000 in PBS for 1 h at 37° C. A substrate solution, o-phenylenediamine dihydrochloride (Sigma), was added and the $OD_{450}$ was determined by ELISA reader.

For the determination of antibodies against coated molecules in chicken sera following i.m. injection of modified hIgG, the sera were tested by the procedure described above, except that the antigen coating the ELISA plate was hIgG modified with the same molecule (coated hIgG) that was injected into the tested chickens.

Fluorometric Assay.

To determine whether MBA-modified hIgG is recognized by the Fc receptor in monocyte cells, the binding efficiency of THP-1 monocytic cells (ATCC: TIB-202) to antigen-bound modified hIgG was tested. Black maxisorp 96 flat microwell plates (Nunc) were incubated overnight at 4° C. with TT protein diluted in carbonate-coating buffer (pH 9.6) to a final concentration of 1 μg/ml, followed by three washes with 0.05% Tween-20 in PBS (wash buffer) and drying on a paper towel. PBS with 5% skim milk was added for 1.5 h at 37° C. as a blocking step. The plate was washed three times with wash buffer and 100 μl of hIgG or MBA-modified hIgG was added at a concentration of 40 μg/ml and incubated for 2 h at 37° C. The plate was then washed three times with wash buffer and 200 μl of THP-1 cells dyed with carboxyfluorescein succinimidyl ester (CFSE) (Invitrogen) at a concentration of $2 \times 10^5$ cells/ml were added and incubated at 37° C., 5% $CO_2$ for 10, 30, or 60 min. At the end of the incubation, the medium and 100 μl of sterile PBS was added. The fluorescence level was determined by fluorometer (Victor3, PerkinElmer Life Sciences) at 535 nm.

Viper Venom-Binding Capability of Coated hsIgG.

The binding of the coated MBA-hsIgG to viper venom as compared to that of unmodified hsIgG by Western Blot Analysis. Electrophoresis was performed on 8-16% gradient polyacrylamide gel (Geba gel). The Venom (10 μl) was mixed with loading buffer (0.5 M Tris HCl pH 6.8, 33% glycerol, 3% SDS, 5% mercaptoethanol, 0.5% bromophenol blue) and the samples were run at RT at 160 Volts in running Buffer (Amresco). The gel was transferred to nitrocellulose membrane, Hybound C (Amersham). Each of the following steps was followed by three washes with 0.05% Tween-20 in PBS. Blocking buffer was added (5% Skim milk, 0.05% Tween-20 in PBS) for 1 hour at 37° C. as a blocking. 20 μg of hsIgG or hsIgG-MBA diluted in blocking buffer were applied and the membrane was incubated for 1 hour at 37° C., following incubation with a 1:5000 dilution of goat anti-hsIgG HRP-conjugated (Sigma) or 1:2000 dilution Avidin-HRP conjugated (Sigma) respectively, for 1 hour at 37° C. in blocking buffer. Bands were detected by enhanced chemiluminescence (ECL) (Pierce).

hsIgG HRP Conjugation.

The conjugation of hsIgG to HRP was as follow; 1 mg of anti-viper venom hsIgG was diluted in phosphate buffer (PB) (25 mM sodium phosphate pH 5.5 mM, Sigma), and mixed with 1 mg Adipic acid dihydrazide (Sigma), and 1 mg of N-(3-Dimethylaminopropyl)-N'-ethylcarbodiimide hydrochloride (EDC) (Fluka). The solution was stirred for 3 hours at room temperature (RT) and then excess reagent was removed by filtration through an Amicon ultra-centrifugal filter device (MWCO 30,000). The filtrate was then diluted in PB and 1 mg of peroxidase (Sigma) was in addition to 1 mg of EDC. The solution was stirred for 3 hours at room temperature (RT) and then excess reagent was removed by filtration as before.

Competitive ELISA.

To evaluate the affinity of anti-viper venom hsIgG-MBA to the antigen, ELISA plate was coated with 1 μg/ml of viper venom. Thereafter, 10 μg/ml of hsIgG-HRP conjugated (constant hsIgG-HRP concentration) mixed with hsIgG, hsIgG-MBA or hsIgG-PEG at serial twofold dilutions (0-100 μg/ml) and added to the plate for 1 h at 37° C., followed by substrate addition. OD values were detected at 450 nm by ELISA reader.

To evaluate the affinity of Trastuzumab-MBA to the antigen, $3*10^4$ of SKBR-3 cells/well incubated for 24 h in 96 wells tissue culture, optic bottom, plate (Nunc). Each of the following steps was followed by three washes with 0.05% Tween-20 in PBS and drying on a paper towel. The cells were fixated to the wells with 4% formaldehyde in PBS for 20 min at R. T. 10 μg/ml of Trastuzumab-fluorescein conjugated (NHS-Fluorescein (Pierce)) mixed with Trastuzumab or Trastuzumab-MBA at twofold serial dilutions (0-100 μg/ml) and added to the plate for 1 h at 37° C., followed by substrate addition. Fluorescent units values were detected at ex/em 490/530 nm by multilable counter 1420 reader (PerkinElmer).

In Vitro Viper Venom Proteolitic Activity Inhibition.

The ability of the coated or uncoated hsIgG to inhibit proteolitic activity by venom was conducted with Azo dye-impregnated collagen (Azocoll) (Sigma). Seventy five mg of azocoll were suspended in 50 ml of PBS, stirred for 2 h at RT and centrifuge at 10,000×g for 10 min, following suspension in 50 ml PBS—This washing step was repeated twice. 200 μg of hsIgG, hsIgG-MBA or hsIgG-PEG were incubated with 50 µg of viper venom for 30 min at 37° C. following addition of 400 µl washed azocoll and incubation for 2 h at 37° C. The reactions were centrifuge and supernatant transferred to 96 wells plate. OD values were detected at 550 nm by ELISA reader.

Evaluation of Venom Neutralization.

The LD50 value for *Vipera palaestinae* venom in Balb/c mice (18-20 g) by the i.v. route was determined by challenging unprotected mice with various doses of crude venom in saline. The results revealed an LD50 value of 1 mg/kg body weight. The neutralizing ability of coated or uncoated hsIgG was assessed by pre-incubation of 200 µg of antivenom with 2 LD50 doses of the venom at 37° C. for 30 min before injecting to three groups of mice (6 in each group) through the i.v. route. The animals were kept under observation for 48 h, afterward number of deaths occurring within 48 h was scored.

Cell Culture.

Human breast cancer cell lines SKBR-3 and BT 474 were purchased from the American Type Tissue Culture Collection. BT 474 was maintained in DMEM with 4.5 g/l glucose, and SKBR-3 was maintained in McCoy's 5A. All cells lines were supplemented with 10% FBS and incubated at 37° C. in a 5% humidified $CO_2$ atmosphere.

Example 1. Coating hIgG with MBA

The reaction of MBA with the antibody was designed to proceed through binding to the amino acid side chains of the protein, i.e. lysine and arginine, to form an imine bond which was then further reduced using cyanoborohydride to form a more stable, non-reversible type of bond. The ratio between MBA and protein was controlled by changing the amount of MBA during its reaction with the antibody, from 20 to 1000 µg of MBA/mg antibody. The molecular ratio of MBA to antibody in the coated protein was monitored by detecting the amount of free amino groups left on the protein relative to uncoated hIgG (see Materials and Methods), using a known method with some modifications for small-scale sampling (96 wells) (Vidal, J. and C. Franci (1986) J Immunol Methods 86(1): 155-6). The findings from these experiments are summarized in Table 2.

TABLE 2

Molecular ratio of MBA to antibody

| Lane no. in FIG. | Free amino groups[1] (µM) | hIgG (µM) | No of free amino groups[2] |
|---|---|---|---|
| 1 | 53.84 | 5.355 | 10.05 |
| 2 | 53.55 | 5.923 | 9.04 |
| 3 | 24.57 | 5.481 | 4.48 |
| 4 | 13.26 | 5.197 | 2.55 |
| 5 | 94.42 | 6.490 | 14.55 |

[1]Based on glycine calibration curve
[2]Calculated

The number of accessible amino groups reacting with the chromophore reagent TNBSA in the native hIgG amounted to 14 or 15 amino residues. Reaction of the antibody with 20 µg MBA/mg blocked 4 to 5 of the protein's amino groups, leaving the other 10 groups free. At a ratio of 1000 µg MBA/mg hIgG, 11 to 12 of the protein's amino groups reacted with the MBA and only 2 or 3 amino groups remained unattached. Glycine was reacted with TNBSA in order to construct a calibration curve. These results were further confirmed by gel electrophoresis of the coated/uncoated hIgG, which showed the same trend, i.e., a gradual increase in the MW of the modified hIgG correlated to an increase in the number of MB As per hIgG molecule (FIG. 1).

Figure 2:
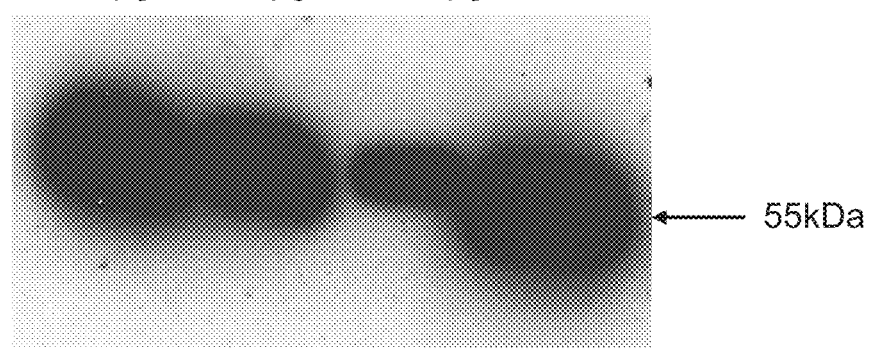

We then tested secondary antibody recognition of hIgG modified with various amounts of MBA (80-1000 µg MBA/mg hIgG) by western blot analysis. Samples (5 µg) were run on a 15% polyacrylamide gel and transferred to nitrocellulose for detection of modified hIgG with HRP-conjugated goat anti-hIgG antibodies. The results, summarized in FIG. 2, demonstrate the correlation between increased number of MBAs per molecule of hIgG and reduced recognition of modified hIgG by the secondary antibody.

Figure 3:
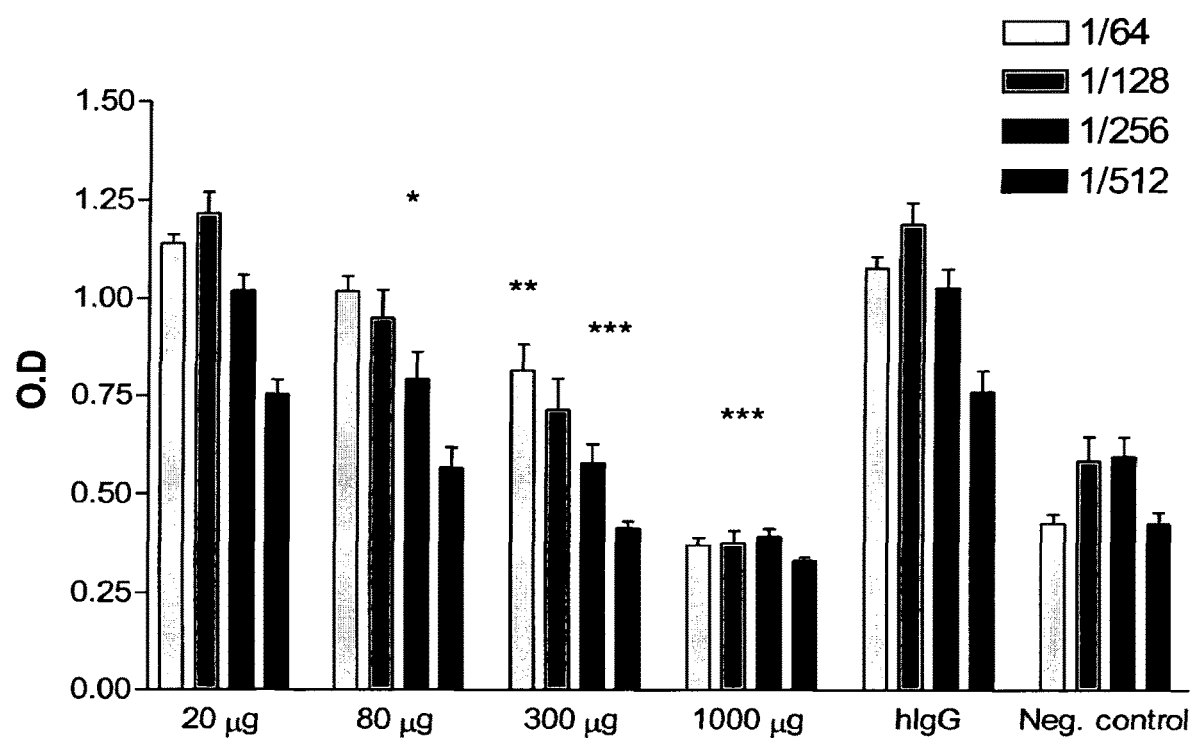

Example 2. Immunogenic Response of Chicken to hIgG Coated with Different Amounts of MBA hIgG antibody was reacted with various concentrations of MBA to examine the immunogenic response of chickens to different levels of MBA coating (see Materials and Methods): 20 µg MBA (hIgG-MBA$^{20}$), 80 µg MBA (hIgG-MBA$^{80}$), 300 µg MBA (hIgG-MBA$^{300}$) and 1000 µg MBA (hIgG-MBA$^{1000}$). Coated or uncoated hIgG (50 µg) was injected twice into chickens i.m., at a 2-week interval. Two weeks after the second injection, blood was drawn and serum was separated and tested by ELISA for antibody production against hIgG. The results, shown in FIG. 3, demonstrate the correlation between increasing number of MB As per molecule of hIgG and decreasing production of antibodies against hIgG in chickens. The immunological response against hIgG was significantly suppressed in chickens injected with hIgG-MBA$^{80}$, hIgG-MBA$^{300}$ and hIgG-MBA$^{1000}$ (FIG. 3). Moreover, the level of antibodies against hIgG in the serum of chickens injected with hIgG-MBA$^{1000}$ was similar to the negative control (non-injected chickens), suggesting abolishment of hIgG antigenicity. Based on these results, a 1:1 ratio (initial weight/weight) of MBA to hIgG was chosen for further experiments.

Figure 4A:
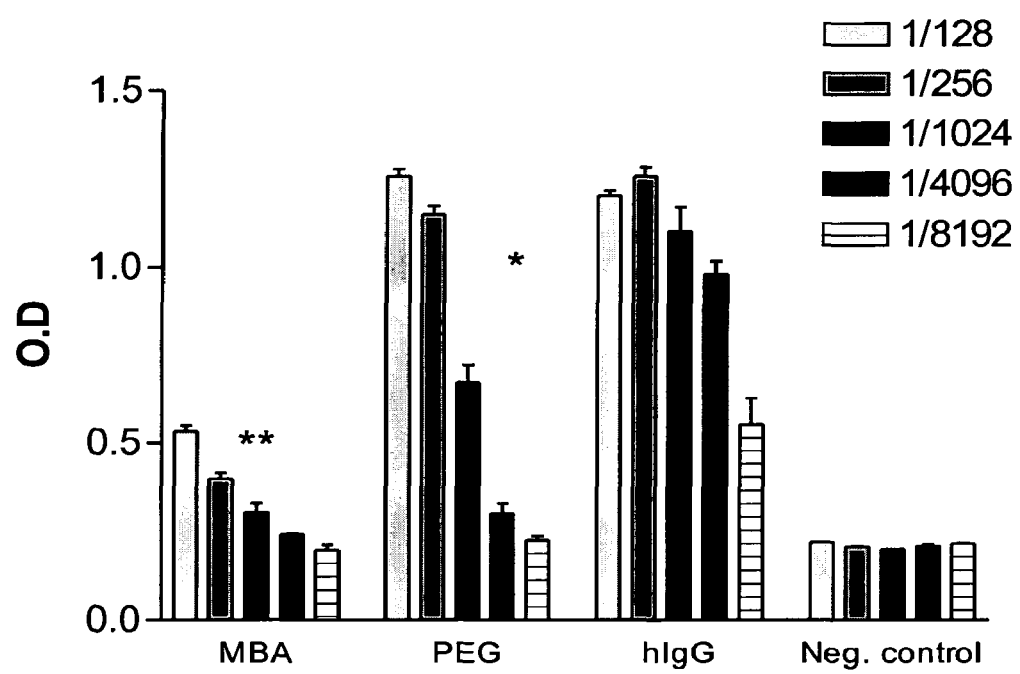
Figure 4B:
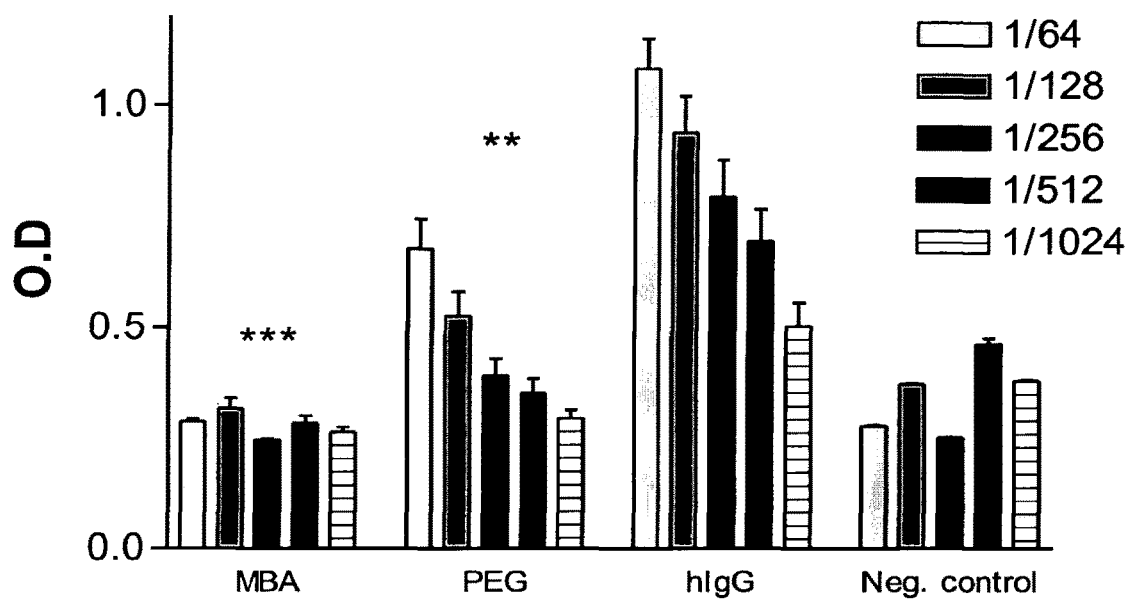

Example 3. Immunological Response in Chickens to hIgG Coated with MBA Vs. PEG and Injected in the Presence or Absence of Adjuvant PEGylation is known to suppress protein immunogenicity and antigenicity (Kubetzko et al., 2005; Veronese and Pasut, 2005; Pasut et al., 2006; Gamez et al., 2007). To compare the masking ability of MBA to that of PEG, 50 µg of hIgG, hIgG-MBA$^{1000}$ or hIgG-PEG were injected into chickens i.m. twice, in the absence or presence of adjuvant, at a 2-week interval. In the case of injection with adjuvant, samples were mixed with Freund's adjuvant to induce a maximal immune response (see Materials and Methods). Two weeks after the second injection, blood was drawn and serum separated and tested for antibody production against hIgG by ELISA. hIgG-PEG was used as a control for immune response suppression to the antigen (hIgG). FIGS. 4A and 4B shows the results for injection in the absence or presence of adjuvant, respectively. Modification with MBA suppressed the immune response to hIgG more effectively than PEGylation in both cases. It is important to note that hIgG coated with biotin or mannose alone did not prevent antibody production against hIgG (data not shown). In the sera of chickens injected with hIgG-MBA$^{1000}$ without adjuvant, the level of antibodies against hIgG was similar to that in the non-injected chickens (negative control). Coating with MBA reduced the immunogenic response against hIgG by an estimated 32-fold relative to non coated hIgG, whereas PEGylation decreased it only fourfold in the absence of adjuvant (FIG. 4A). Results summarized in FIG. 4B demonstrate that hIgG-PEG injected together with adjuvant produced an antibody titer similar to that with uncoated hIgG (positive control) at a 1:128 and 1:256 dilution; its masking effect was only observed at a 1:1024 dilution. On the other hand, in chickens injected with hIgG-MBA$^{1000}$ in the presence of adjuvant, the immune response against hIgG was significantly reduced, even at low dilution (1:128). According to our estimation, injection with hIgG-MBA$^{1000}$ decreased the immunogenic response against hIgG 32-fold while injection with hIgG-PEG decreased antibody production only eightfold, relative to controls injected with uncoated hIgG.

Example 4. Examination of MBA Immunogenicity in Chickens

Figure 5:
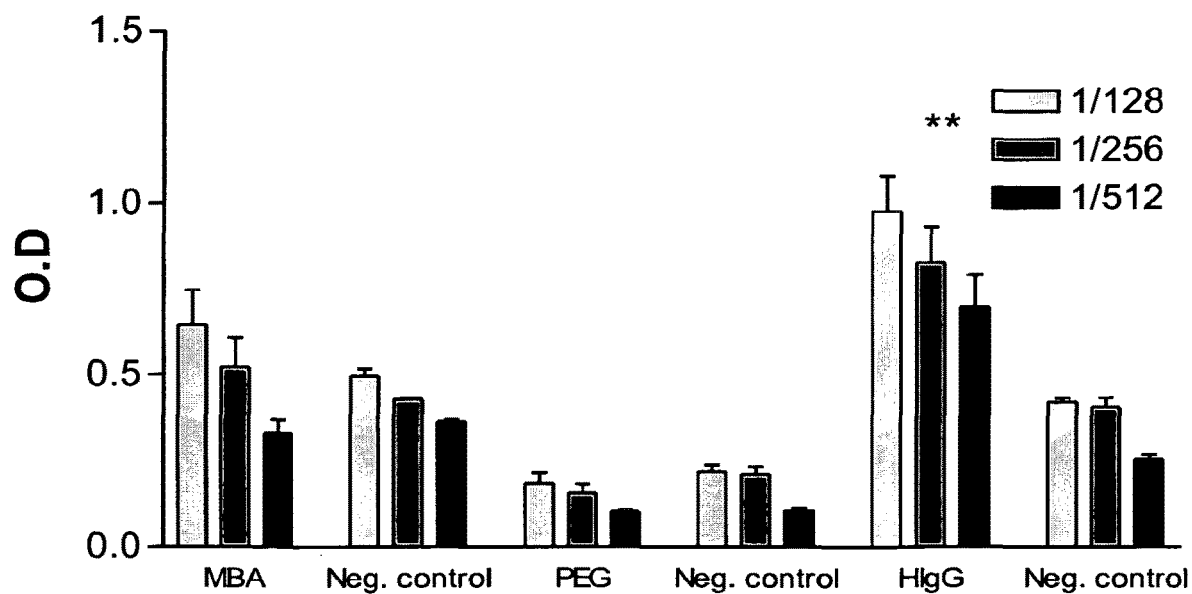

To determine whether the MBA molecule is itself immunogenic when conjugated to the antigen or if MBA bound to antibody induces production of antibodies against the hIgG-MBA construct, sera from chickens injected with hIgG, hIgG-MBA$^{1000}$ or hIgG-PEG in the absence of adjuvant (see above and FIG. 4A) were analyzed by ELISA. Serum from chickens injected with hIgG-MBA$^{1000}$ was examined on hIgG-MBA$^{1000}$, whereas serum from chickens injected with hIgG-PEG was tested on hIgG-PEG and so on. The level of antibodies against MBA and/or the hIgG-MBA$^{1000}$ construct in serum from chickens injected with hIgG-MBA$^{1000}$ was not significantly different from the negative control (serum from non-injected chickens on hIgG-MBA$^{1000}$) (FIG. 5). These results indicate that, similar to PEG, neither MBA molecules nor hIgG coated with MBA are immunogenic in chickens.

Example 5. Immune Response in Mice to Chicken IgY Coated with MBA or PEG

Chicken immunoglobulin, isolated from egg yolk (IgY) was coated with MBA or PEG 5000, and injected to mice intravenously (IV) or intramuscularly (IM). Antibody response to the coated immunoglobulin, and to the coated molecules was determined by ELISA. Following one injection the antibody response to IgY was reduced 4-fold (IV) and 2-fold (IM) by MBA, while the response to PEG was increased, as compared to non-coated IgY (FIGS. 6A-B).

Example 6. Antibody Response to Coated or Uncoated hsIgG

MBA masking ability was tested and compared to both PEG 5 kDa and 20 kDa following i.m. or i.v. injection of 50 µg of hsIgG, hsIgG-MBA, hsIgG-PEG to Balb/c and C57BL6 mice three times at a 2-weeks interval.

Two weeks after each injection, blood was drawn and serum was separated and tested for antibody production against hsIgG by ELISA.

In Balb/c mice, MBA was found to reduce the immune response to hsIgG significantly as compared to uncoated or PEGylated hsIgG in both administration routes (FIG. 7A and Table 2). In this experiment, masking ability of PEG 5 was superior to PEG 20 molecule.

A similar effect was found in C57BL6 mice; the MBA molecule was found to be superior to PEG in its masking capabilities and, significantly reduced the immune response

TABLE 3

Folds of reduction in antibody response to antigen due to MBA masking as compared to PEG-coated or uncoated hsIgG.

| Route of administration | Treatment | First injection | | Second injection | | Third injection | |
| --- | --- | --- | --- | --- | --- | --- | --- |
| | | Balb/C | C57BL6 | Balb/C | C57BL6 | Balb/C | C57BL6 |
| i.m. | IgG | 4 | 20 | 20 | 45 | 15 | 51 |
| | IgG-PEG | 3 | 10 | 6 | 2 | 3 | 7 |
| i.v. | IgG | 13 | 22 | 158 | 62 | 57 | 47 |
| | IgG-PEG | 9 | 21 | 57 | 2 | 20 | 2 |

Humoral Immune response, in Titer-folds reduction, of MBA coated vs. PEG 5 coated or uncoated IgG. The reduction fold depict in two different mice inbred strains (Balb/c and C57BL6) and in two routes of administration (i.m. and i.v.). to hsIgG in both administration routes (FIG. 7B and Table 2).

Example 7. Immunological Humoral Response Against Anti-Venom after Sequential Dose Treatment In order to imitate sequential anti-venom dose treatment, mice were injected with 200 µg of hsIgG anti-venom in 3 days (i.e. 25 µg, 75 µg, and 100 µg a day respectively). Two weeks after the third injection, bloods were drawn and antibody level against hsIgG was tested by ELISA. Mouse antibody titer against anti-venom was significantly lower in mouse treated with masked anti-venom (FIG. 8). Coating with MBA reduced the humoral response against hsIgG by an estimated 15 and 12 fold relative to unmodified hsIgG in i.m. route and i.v. respectively. When comparing to PEGylated hsIgG, coating with MBA reduced the humoral immune response against hsIgG by 4 fold, in i.m. and i.v. injection route.

Example 8. Activity of Modified Antibodies 8.1 Determination of Inhibition of Snake Venom Activity by Coated Antibody Snake venom is composed of several enzymes. The inhibition of the activity of two of these enzymes involved in hemolysis and fibrinogen degradation, was determined. The coating of anti-C. atrox venom IgY did not affect the ability of the antibody to inhibit hemolysis and inhibit more efficiently venom influence on clotting time. Following masking with MBA or PEG, the anti-venom IgY antibodies inhibit the hemolysis similar to unmodified antibodies (Table 4) and the inhibition of fibrinogen degradation by the antibody was increased (Table 5).

8.2 Binding of MgG-MBA$^{1000}$ to Monocytic THP-1 Cells

To examine recognition of coated hIgG by the Fc receptor, the coated antibodies bound to their antigen

TABLE 4

Effect of anti-venom coated IgY on RBC hemolysis

| S. no | Sample | OD 405 nm |
|---|---|---|
| 1 | Control plasma | 0.315 |
| 2 | Plasma + 20 μg venom | 0.7435 |
| 3 | Plasma + 20 μg venom + 1 mg IgY | 0.428 |
| 4 | Plasma + 20 μg venom + 2 mg IgY | 0.26 |
| 5 | Plasma + 20 μg venom + 1 mg IgY-MBA | 0.4215 |
| 6 | Plasma + 20 μg venom + 2 mg IgY-MBA | 0.283 |
| 7 | Plasma + 20 μg venom + 1 mg IgY-PEG | 0.3185 |
| 8 | Plasma + 20 μg venom + 2 mg IgY-PEG | 0.2805 |

TABLE 5

Effect of anti-venom coated IgY on the clotting time of human plasma

| S. no | Sample | Thrombin time | % change from control |
|---|---|---|---|
| 1 | Control plasma | 21 | — |
| 2 | Plasma + 20 μg venom | 150 | 614 |
| 3 | Plasma + 20 μg venom + 1 mg IgY | 138 | 557 |
| 4 | Plasma + 20 μg venom + 2 mg IgY | 138 | 557 |
| 5 | Plasma + 20 μg venom + 1 mg IgY-MBA | 82 | 290 |
| 6 | Plasma + 20 μg venom + 2 mg IgY-MBA | 80 | 280 |
| 7 | Plasma + 20 μg venom + 1 mg IgY-PEG | 60 | 185 |
| 8 | Plasma + 20 μg venom + 2 mg IgY-PEG | 50 | 138 |

Figure 9:
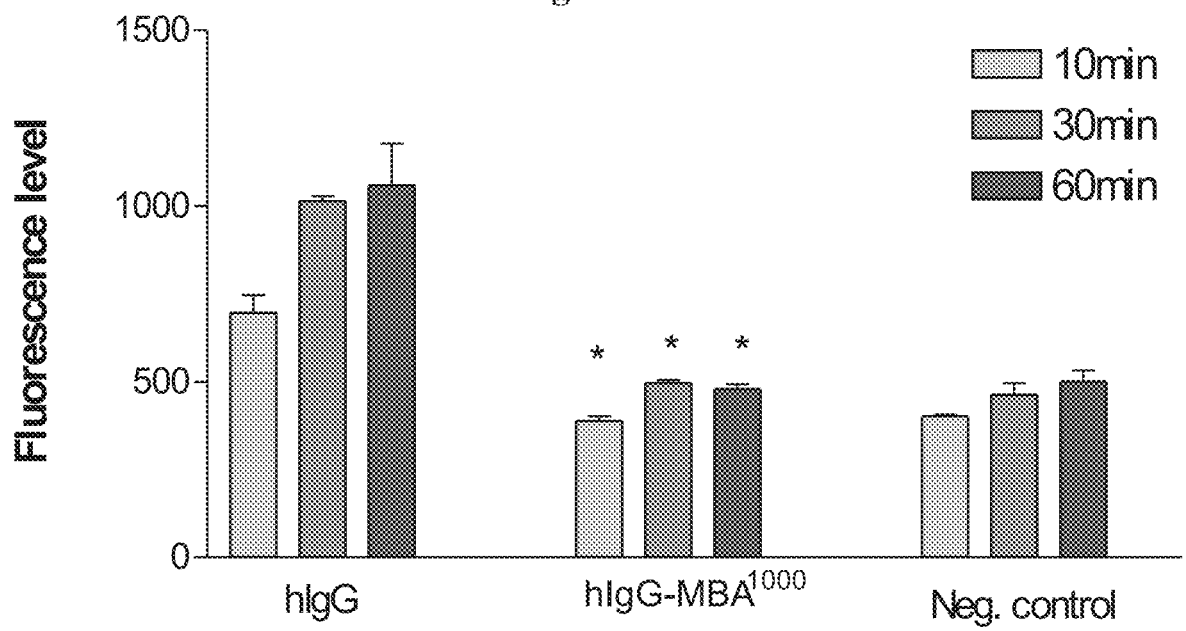

(TT) were tested. An ELISA plate with hIgG or hIgG-MBA$^{1000}$ bound to TT antigen was incubated with fluorescent THP-1 cells for different periods of time. Fluorescence level was determined by fluorometer after 10, 30 and 60 min of incubation with the cells. TT without hIgG was used as a negative control. Results, summarized in FIG. 9, showed that the fluorescence level in wells with hIgG-MBA$^{1000}$ was similar to that in wells without TT-bound antibodies (negative control). These results indicate that coating hIgG with MBA fully abrogates recognition of the antibody by the monocytic cells.

Figure 10:
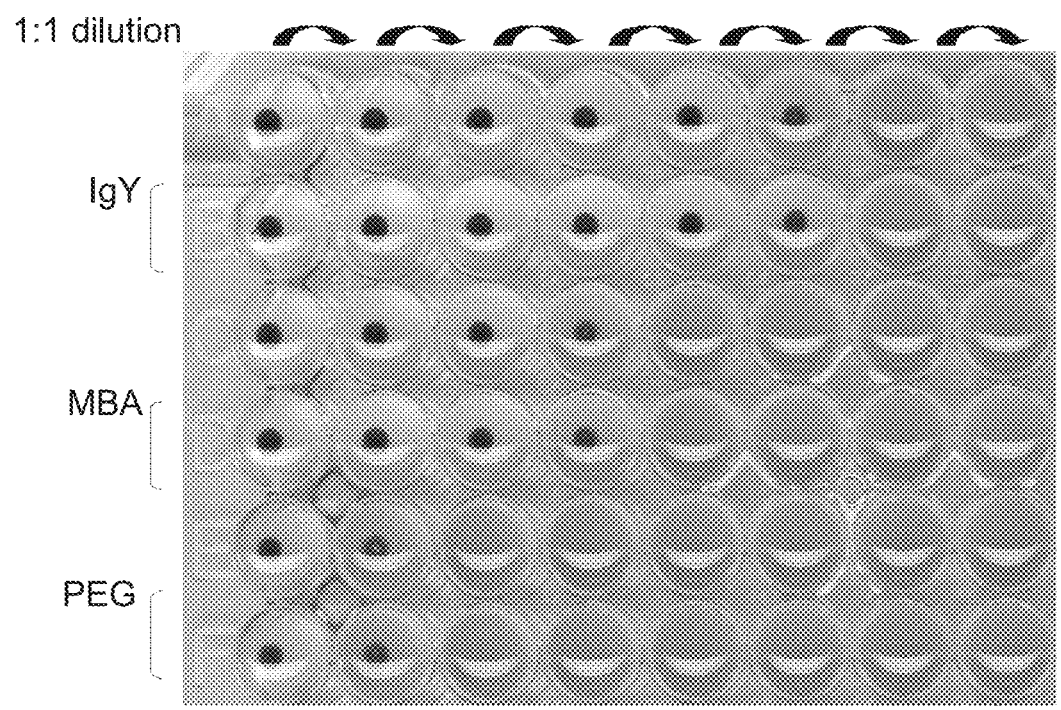

8.3 Determination of Coated Antibody Hemmaglutination Inhibition (HI) Activity Inhibition of hemagglutination of red blood cells by anti-influenza antibodies (ALA) was found to be in correlation with virus neutralization. ALA derived from hyperimmune sera were coated with PEG or MBA, and tested for hemagglutination inhibition (HI). Coated anti-influenza antibodies retain the ability of HI, but MBA and PEG coating decrease the HI 4 and 16 fold, respectively (FIG. 10).

8.4 Binding Capability of MBA Coated hsIgG to the Antigen

8.4a Multi Antigen Detection by Coated hsIgG

Figure 11:
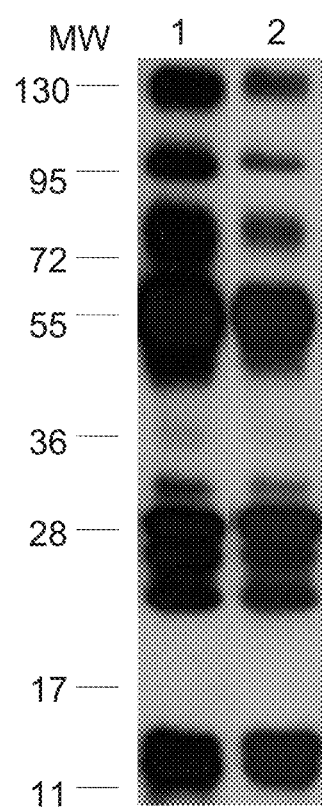

Anti venom horse IgG is a set of polyclonal Abs against a set of venom proteins. Coating a set of polyclonal Abs may possibly affect the detection of particular antigen by specific Abs. To test coated antivenom antibodies with *V. palaestinae* venom, different amounts of the venom were immunoblotted with hsIgG or with hsIgG-MBA. Immunoblotting showed detection of all major protein bands in the venom with coated or uncoated antivenoms (FIG. 11). The results suggest that coating with MBA, did not impair the detection of any venom antigen. The intensity variation of the bands between the coated and uncoated antibodies cannot be compared, due to different detection methods by the second antibody.

8.4B Binding Affinity of hsIgG Coated with MBA or with PEG

Figure 12:
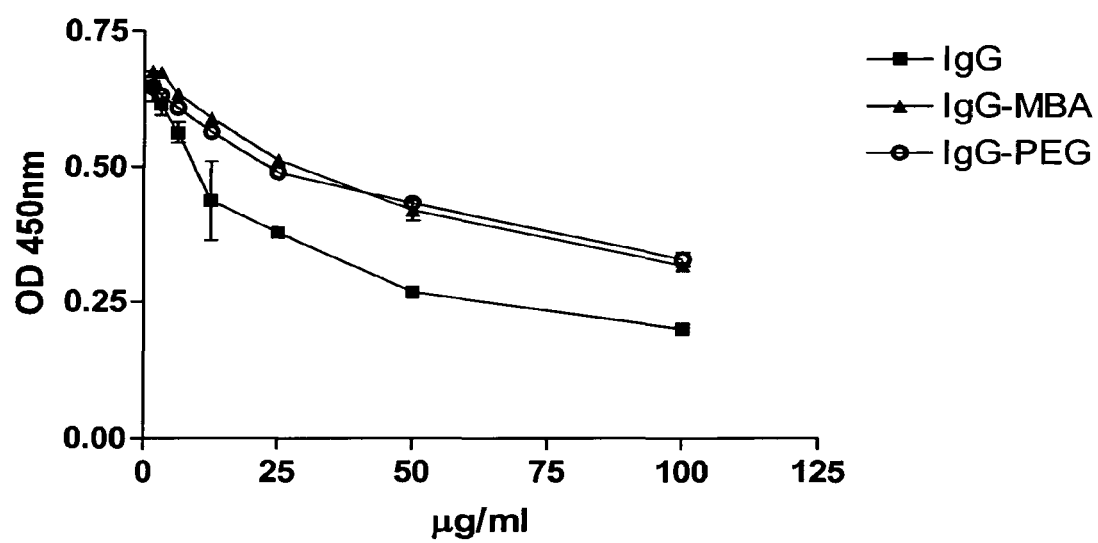

To evaluate the binding affinity of coated horse antivenom to the venom, competitive ELISA was conducted. ELISA plate was coated with viper venom and incubated with constant concentration of hsIgG-HRP mixed with twofold serial dilutions of non-modified hsIgG, hsIgG-MBA or with hsIgG-PEG. Thereafter, the plate was incubated with HRP substrate, followed by ELISA reader detection. According to the results, summarized in FIG. 12, the affinity of the modified hsIgG was slightly but not significantly lower from that of the uncoated hsIgG. Antibodies coated with MBA and PEG show identical affinity to antigen.

8.4C Venom Protease Activity Inhibition by Coated or Uncoated hsIgG

Figure 13:
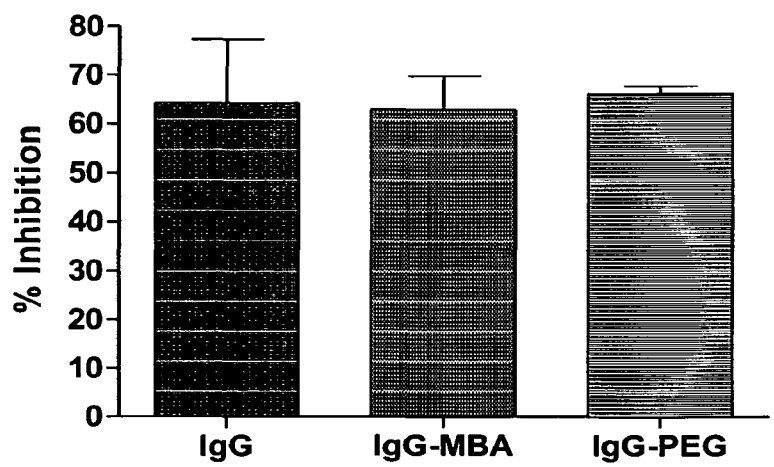

To examine whether coated antivenom could inhibit protease activity similarly to the uncoated antivenom in vitro, Azocoll protease activity assay was performed. The assay relies on the ability of the venom enzyme to digests dye-impregnated collagen and by that, releasing the dye to the supernatant. 50 μg of the venom were pre-incubated with 200 μg of hsIgG, hsIgG-MBA or with hsIgG-PEG and added to Azocoll reagent. Thereafter, absorbance of supernatants was monitored. FIG. 13 shows that coating of antivenom hsIgG by MBA does not reduce the antivenom inhibition activity of the antibody.

Example 9. Activity of Modified Anti-Venom Horse Antibodies In Vivo

9.1

Figure 14:
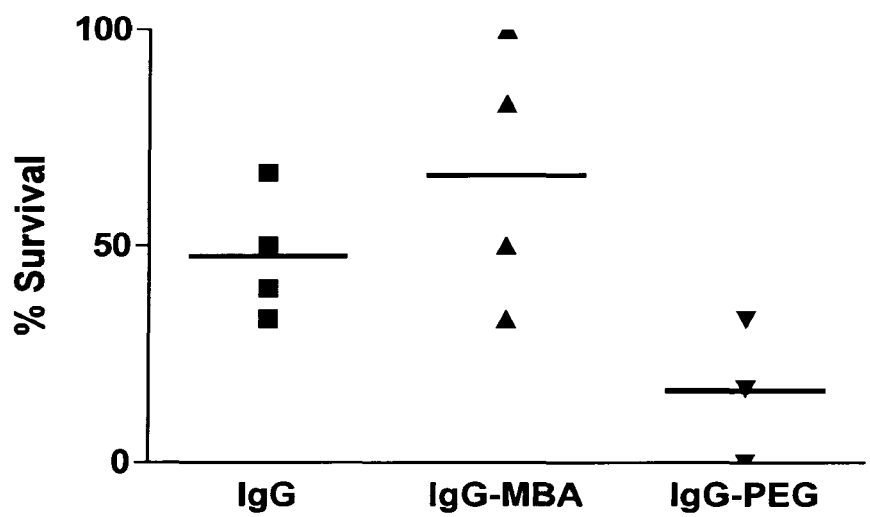
Figure 15:
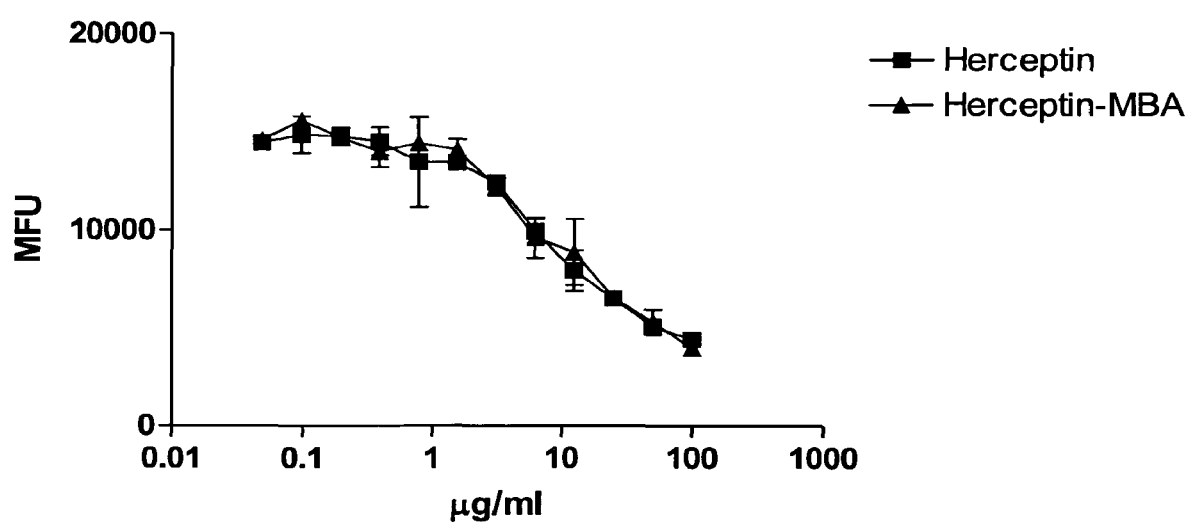
Figure 16:
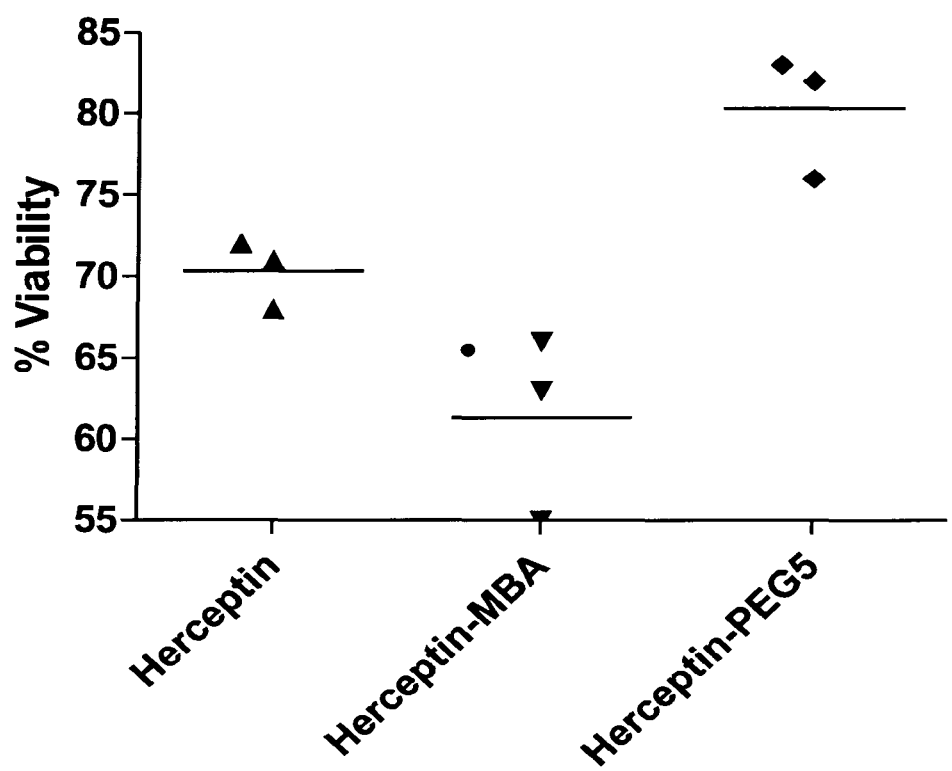

Venom neutralization in vivo by coated or uncoated anti-venom. To determine the effect of coating procedure of anti-venom to the efficacy of *V. palaestinae* venom neutralization, a neutralization test of venom lethality by hsIgG was performed in vivo. 2× lethal dose (30 μg) of venom were pre-incubated with 200 μg of coated or uncoated anti-venom for half an hour and injected i.v. into Balb/c mice. Neutralization ability was calculated from the number of deaths occurring within 48 hour subsequent to injection. Anti-venom coated with MBA did not impair venom neutralization in vivo (FIG. 14). Rather, the group treated with MBA coated anti-venom had lower death events within the group although not significantly, the difference is consistent compared to uncoated or PEG coated antivenom.

9.2. Immunological Humoral Response Against Anti-Venom, Following Neutralization Test To evaluate the immune response evoked by hsIgG antivenom, in mice which survived the neutralization test, bloods were drawn two weeks after the neutralization test and sera were separated and tested for antibody production against hsIgG by ELISA. Masking antivenom with MBA evoked at least 10 fold lower humoral immune response then uncoated or PEG-coated hsIgG (Table 6).

TABLE 6

Immune response against IgG following neutralization test

| Neutralization treatment | Anti hsIgG titer | Anti MBA titer |
|---|---|---|
| IgG | 2048 | — |
| IgG-MBA | <256 | <128 |
| IgG-PEG | 2048 | — |

Immune response was evaluated in mouse which survive neutralization test. Blood was drawn two weeks after challenge end. Results are from two independent tests.

Example 10. Effect of MBA Coating on Monoclonal Therapeutic Antibodies

In order to evaluate the effect of MBA coating on monoclonal antibodies, we chose Trastuzumab (herceptin) as a candidate. Trastuzumab is a humanized anti-HER2 monoclonal antibody directed against the HER2 protein (p185HER2/neu), which is the product of the HER2 proto-oncogene (also designated as c-erbB-2 or HER2/neu). HER2 is overexpressed in approximately 20% to 25% of breast tumors. This alteration is associated with poor prognosis and may affect the response to hormonal therapy and chemotherapy. Trastuzumab demonstrated a benefit as a single agent in first- or second-line treatment of HER2-overexpressing (HER2+) metastatic breast cancer (MBC) (Vogel et al 2002).

Exposure of human breast cancer cell lines, which express high levels of endogenous HER2 receptor, to Trastuzumab, inhibit cell proliferation.

Here, we tested the effect of MBA masking of Trastuzumab on the antibody activity in vitro.

FIG. 15 shows a competitive ELISA in which plates have been coated with cells expressing HER2. As can be clearly seen, the coating of Trastuzumab with MBA did not affect its binding affinity towards its native antigen.

The efficiency of the Trastuzumab to kill cancer cells is not adversely affected by coating with MBA. In a viability test, cancer cells ($5\times10^3$ per well) were seeded onto a 96-well plate. The survival of these cells after treatment with coated/uncoated 10 μg/ml trastuzumab for 5 days at 37° C. in a 5% humidified $CO_2$ atmosphere was determined using the Cell Titer-blue Luminescent Cell Viability Assay reagent (Promega) following the supplier's instructions. Fluorescent units was measured by DTX 880 Multimode Detector (Beackman Coulter).

As can be seen in FIG. 16, exposure of the cells to MBA-modified Trastuzumab reduced the viability of the cells to about 60% as compared with 70% and 80% for unmodified Trastuzumab and pegylated Trastuzumab, respectively. Thus, Trastuzumab-MBA coated antibody retains its activity as compared to uncoated Trastuzumab antibody.

REFERENCES

Buchwald, U. K., and L. Pirofski. (2003) Immune therapy for infectious diseases at the dawn of the 21st century: The past, present and future role of antibody therapy, therapeutic vaccination and biological response modifiers. Curr. Pharm. Des. 9:945-968.

Gaberc-Porekar, V., I. Zore, et al. (2008). "Obstacles and pitfalls in the PEGylation of therapeutic proteins." Curr Opin Drug Discov Devel 11(2): 242-50.

Gamez, A., L. Wang, et al. (2007). "Structure-based epitope and PEGylation sites mapping of phenylalanine ammonia-lyase for enzyme substitution treatment of phenylketonuria." Mol Genet Metab 91(4): 325-34.

Harris L C, Davis P J, James D C. (2003) Fatty acids as haptens: exploring the limits of antigenicity. Mol Immunol. 2003 October; 40(6):381-9.

Kobayashi, K., A. Hirano, et al. (2001). "Reduced immunogenicity of beta-lactoglobulin by conjugation with carboxymethyl dextran differing in molecular weight." J Agric Food Chem 49(2): 823-31.

Kubetzko, S., C. A. Sarkar, et al. (2005). "Protein PEGylation decreases observed target association rates via a dual blocking mechanism." Mol Pharmacol 68(5): 1439-54.

Mehvar, R. (2003). "Recent trends in the use of polysaccharides for improved delivery of therapeutic agents: pharmacokinetic and pharmacodynamic perspectives." Curr Pharm Biotechnol 4(5): 283-302.

Ong G L, Ettenson D, Sharkey R M, Marks A, Baumal R, Goldenberg D M, Mattes M J. (1991) Galactose-conjugated antibodies in cancer therapy: properties and principles of action. Cancer Res. 1991 Mar. 15; 51(6): 1619-26.

Pasut, G., M. Margherita, et al. (2006). Basic strategies for PEGylation of peptide and protein drugs. Delivery of Protein and Peptide Drugs in Cancer. V. T. Torchilin. Northeastern University, USA.

Veronese, F. M. and G. Pasut (2005). "PEGylation, successful approach to drug delivery." Drug Discov Today 10(21): 1451-8.

Vidal, J. and C. Franci (1986). "Re.: Trinitrophenyl-protein conjugates are more complex than it is currently thought." J Immunol Methods 86(1): 155-6.

Vogel C L, Cobleigh M A, Tripathy D, Gutheil J C, Harris L N, Fehrenbacher L, Slamon D J, Murphy M, Novotny W F, Burchmore M, Shak S, Stewart S J, Press M. Efficacy and safety of trastuzumab as a single agent in first-line treatment of HER2-overexpressing metastatic breast cancer. J Clin Oncol. 2002; 20:719-726.

The invention claimed is:

1. A pharmaceutical compositions comprising a masked protein which comprises an immunogenic protein directly covalently linked to a non-immunogenic molecule so as to result in a masked protein whose immunogenicity is decreased relative to that of the immunogenic protein, said non-immunogenic molecule is selected from 2-amino-mannose-biotin adduct, a 2-amino-mannose-desthiobitin adduct and a 2-amino-mannose-lipoic acid adduct, wherein the 2-amino group of amino-mannose is directly linked to the carboxyl group of biotin, desthiobitotin or lipoic acid forming an amide bond, and said immunogenic protein is directly covalently linked, via a free amino or a free carboxyl group of said immunogenic protein, to said 2-amino-mannose.

2. The pharmaceutical composition according to claim 1, wherein said immunogenic protein is an immunogenic antibody.

3. The pharmaceutical composition according to claim 2, wherein said immunogenic antibody is selected from the group consisting of (i) a humanized or chimeric monoclonal IgG antibody; (ii) a mammalian monoclonal IgG antibody; (iii) a mammalian polyclonal IgG antibody; and (iv) a chicken IgY antibody.

4. The pharmaceutical composition according to claim 3, wherein the antibody is an anti-tumor associated antigen antibody, an anti-snake venom antibody, an anti-virus antibody or an anti-bacterium antibody.

5. The pharmaceutical composition according to claim 4, wherein the immunogenic antibody is an anti-bacterium chicken IgY antibody.

6. The pharmaceutical composition of claim 1 comprising a pharmaceutically acceptable carrier.

7. The pharmaceutical composition according to claim 2, wherein said immunogenic antibody is an anti-bacterium antibody.

8. The pharmaceutical composition according to claim 7, wherein said immunogenic antibody is an anti-bacterium chicken IgY antibody.

9. The pharmaceutical composition of claim 1, wherein the ratio of non-immunogenic molecule to immunogenic protein is between 4:1 and 24:1.

10. The pharmaceutical composition of claim 1, where said masked protein is directly covalently linked to a plurality of 2-amino-mannose biotin adducts, wherein at least one free amino group of said 2-amino-mannose biotin adduct and at least one free carboxyl group of said immunogenic protein, is masked by a second molecule of said 2-amino-mannose biotin adduct, wherein the first and second molecules may be structurally the same or different.

* * * * *